US008021689B2

(12) United States Patent
Reddy et al.

(10) Patent No.: US 8,021,689 B2
(45) Date of Patent: Sep. 20, 2011

(54) NANOPARTICLES FOR IMMUNOTHERAPY

(75) Inventors: Sai T. Reddy, Lausanne (CH); Jeffrey A. Hubbell, Morges (CH); Melody A. Swartz, Morges (CH); André van der Vlies, Zurich (CH)

(73) Assignee: Ecole Polytechnique Federale de Lausanne ("EPFL"), Lausanne (CH)

( * ) Notice: Subject to any disclaimer, the term of this patent is extended or adjusted under 35 U.S.C. 154(b) by 657 days.

(21) Appl. No.: 11/707,627

(22) Filed: Feb. 19, 2007

(65) Prior Publication Data
US 2008/0031899 A1 Feb. 7, 2008

Related U.S. Application Data

(60) Provisional application No. 60/775,132, filed on Feb. 21, 2006.

(51) Int. Cl.
*A61K 9/14* (2006.01)
(52) U.S. Cl. ..................................................... 424/489
(58) Field of Classification Search .................. 424/489
See application file for complete search history.

(56) References Cited

U.S. PATENT DOCUMENTS

| 6,333,051 | B1 | 12/2001 | Kabanov et al. | |
|---|---|---|---|---|
| 6,455,071 | B1 | 9/2002 | Shchepinov et al. | |
| 6,869,935 | B2 | 3/2005 | Hinton et al. | |
| 6,998,115 | B2 | 2/2006 | Langer et al. | |
| 7,026,162 | B2 | 4/2006 | Lo et al. | |
| 7,052,694 | B2 | 5/2006 | Pease et al. | |
| 7,122,354 | B2 | 10/2006 | Selden et al. | |
| 7,157,089 | B1 | 1/2007 | Mizzen et al. | |
| 7,160,695 | B2 | 1/2007 | Bertin et al. | |
| 2004/0086479 | A1 | 5/2004 | Grinstaff et al. | |
| 2004/0247624 | A1 | 12/2004 | Unger et al. | |
| 2006/0057211 | A1* | 3/2006 | Chorny et al. | 424/486 |
| 2006/0204443 | A1 | 9/2006 | Kobayashi et al. | |

OTHER PUBLICATIONS

Bonifaz et al, "In Vivo Targeting of Antigens to Maturing Dendritic Cells via the DEC-205 Receptor Improves T Cell Vaccination", J. Ex. Med., 199(6): 815-824 (2004).
Duncan et al., "Dendrimer biocompatibility and toxicity", Advanced Drug Delivery Reviews, 2215-2237 (2005).
Dutta et al, "Targeting potential and anti-HIV activity of lamivudine loaded mannosylated poly (propyleneimine) dendrimer", Biochimica et Biophysica Acta, 1770(4):681-686 (2007).
Fifis et al., "Size-Dependent Immunogenicity: Thereapeutic and Protective Properties of Nano-vaccines against Tumors" The Journal of Immunology, 173:3148-3154 (2004).
Gadjeva et al., "The Covalent Binding Reaction of Complement Component C3", The Journal of Immunology, 161:985-990 (1998).
Jiang et al., "Biodegradable poly(lactic-co-glycolic acid) microparticles for injectable delivery of vaccine antigens", Advanced Drug Delivery Reviews, 57: 391-410 (2005).
Kidane et al., "Complement Activation of PEO-Grafted Glass Surfaces", J. Biomed Mater Res, 48:640-647 (1999).
Kobayashi et al., "Nano-sized MRI contrast agents with dendrimer cores", Advanced Drug Delivery Reviews, 57:2271-2286 (2005).
Kwon et al., "In vivo targeting of dendritic cells for activation of cellular immunity using vaccine carriers based on pH-responsive microparticles", PNAS, 102(51): 18264-18268, (2005).
Moein Maghimi et al., "Nanomedicine: Current status and future prospects", The FASEB Journal Review, 19:311-330 (2005).
O'Hagan et al., "Recent Advances in the Discovery and Delivery of Vaccine Adjuvants", Nature Reviews, 2: 727-735 (2003).
Pack, "DNA Delivery Timing is Everything", Nature Materials, 3:133-134 (Mar. 2004).
Pashine et al., "Targeting the innate immune response with improved vaccine adjuvants", Nature Medicine, 11(4): S63-S68 (2005).
Patri et al., "Synthesis and in Vitro Testing of J591 Antibody-Dendrimer Conjugates for Targeted Prostate Cancer Thereapy", Bioconjugate Chem., 15:1174-1181 (2004).
Plank et al., "Activation of the complement system by synthetic DNA complexes: a potential barrier for intravenous gene delivery", 12:1437-1446 (1996)(Abstract).
Rehor et al., "Oxidation-Sensitive Polymeric Nanoparticles", Langmuir, 21:411-417 (2005).
Ulevitch, "Therapeutics Targeting the Innate Immune System", Nature Reviews/Immunology, 4:512-520 (2004).
Van Broekhoven et al., "Targeting Dendritic Cells with Antigen-Containing Liposomes: A Highly Effective Procedure for Induction of Antitumor Immunity and for Tumor Immunotherapy", Cancer Research, 64:4357-4365 (2004).
Wang et al., "Molecularly engineered poly(ortho ester) microspheres for enhanced delivery of DNA vaccines", Nature Materials, 3: 190-196 (2004).
Wilson et al., "Most lymphoid organ dendritic cell types are phenotypically and functionally immature", Blood, 102 (6): 2187-2194 (2003).
International Search Report, PCT/US07/04671 dated Jul. 30, 2008.

* cited by examiner

*Primary Examiner* — Michael G Hartley
*Assistant Examiner* — James Rogers
(74) *Attorney, Agent, or Firm* — Dardi & Herbert, PLLC

(57) ABSTRACT

Nanoparticles that activate complement in the absence of biological molecules are described. The nanoparticles are shown to specifically target antigen presenting cells in specifically in lymph nodes, without the use of a biological molecule for targeting. These particles are useful vehicles for delivering immunotherapeutics.

31 Claims, 15 Drawing Sheets

NANOPARTICLES FOR IMMUNOTHERAPY

CROSS REFERENCE TO RELATED APPLICATIONS

This Application claims priority to U.S. Patent Ser. No. 60/775,132 filed Feb. 21, 2006, which is hereby incorporated by reference herein.

TECHNICAL FIELD

The technical field relates, in some aspects, to nanoparticles with surface chemistries for activating the immune system.

BACKGROUND

Many medical benefits could be realized if the immune system could be trained to respond to antigens in a desired manner such as by developing tolerance to the antigen or learning to reject it. Diverse approaches have been attempted to meet this challenge, including systemic drug treatments, injection of antigens, and antibody therapies.

SUMMARY OF THE INVENTION

One new approach, among others disclosed herein, specifically targets therapeutic substances to antigen-presenting cells (APCs) at a specific location in the body. APCs are typically dendritic cells and macrophages and in some cases B cells. Herein, APC is a term used only to describe dendritic cells and macrophages, and excludes B cells. Even though APCs are spread throughout the body, this approach targets the agent to the APCs at a particular location: the lymph node. APCs behave differently at the lymph node as opposed to other parts of the body, so that intake of the agent at this location is advantageous. Further, the vehicle persists over hours or days so that it can accomplish its effects and is also biodegradable. Not only are APCs targeted specifically at the lymph node, but the delivery vehicle for the therapeutic agent activates the APCs in a specific manner: by activating the complement system. Activating the complement system invokes known pathways of response so that appropriate immunotherapeutic agents can be chosen. Moreover, the complement system is activated by synthetic materials in the delivery vehicle without involving biological agents. The result of all of these specially-targeted features is a vehicle that generically delivers a therapeutic agent to APCs at a time and place wherein the APCs are activated to achieve a desired immunotherapy. The vehicle itself does not involve biological molecules or polypeptides so that it is ready to receive any agent without conflict, cross-reaction, or unwanted antagonism of the immune system.

This approach includes, in some embodiments, particles that have suitable physical properties and that are sized to flow through the interstitial spaces to penetrate the lymphatic system. Particles that are too large will not effectively migrate to the lymphatic system. Such particles may be made with biodegradable synthetic polymers and polymers that activate complement. Such particles may be made by crosslinking various polymers together and disposing certain complement-activating functional groups at a location on the particles that is available for complement activation. All of these features are described in detail, below.

In some embodiments, a composition is a nanoparticle composition comprising: an isolated collection of synthetic biodegradable particles associated with an immunotherapeutic agent and comprising a first polymer that activates complement and a second covalently crosslinked polymer, wherein the collection has a mean diameter from about 10 nm to about 100 nm, the first polymer is free of naturally-occurring biomolecules that activate complement, and the first polymer is strongly bound to the second polymer.

Some embodiments relate to a method of making an immunotherapeutic composition of nanoparticles comprising emulsion polymerization of a first polymer with a second polymer that is the emulsifier used during the polymerization to make a collection of biodegradable particles with a mean diameter of between about 20 nm and about 100 nm, choosing the second polymer to comprise hydroxyl functional groups that activate complement, and associating an immunotherapeutic with the particles.

Some embodiments relate to a method of delivering an immunotherapeutic agent, the method comprising introducing into a patient a collection of synthetic biodegradable particles that are specifically targeted to antigen presenting cells in lymph nodes, wherein the particles comprise a first polymer that activates complement, the collection has a mean diameter from about 10 nm to about 100 nm, the first polymer is free of naturally-occurring biomolecules that activate complement, and the particles comprise a second covalently crosslinked polymer that is strongly bound to the first polymer.

Some embodiments relate to a nanoparticle composition comprising an isolated collection of synthetic particles that comprise a synthetic polymer that activates complement, wherein the collection has a mean particle diameter of, e.g., about 10 nm to about 100 nm. The particles may further be associated with an antigen. The synthetic polymer in some embodiments is free of sequences of amino acids or sequences of saccharides that activate complement, or altogether free of amino acids and/or nucleic acids and/or saccharides. The synthetic polymer may include, e.g., comprises a hydrophobic portion that is adsorbed to a hydrophobic portion of a second biodegradable polymer that forms a core of the nanoparticle to thereby bind the synthetic polymer to the core.

Some embodiments relate to nanoparticle composition comprising: an isolated collection of synthetic particles, wherein the collection has a mean diameter of about, e.g., 10 nm to about 100 nm, wherein the particles comprise an immunosuppressant drug, and wherein the particles are further associated with an antigen. In some versions, the particles comprise an amphiphilic block copolymer of at least one hydrophobic block and at least one hydrophilic block, wherein the block copolymer self-assembles in aqueous solutions to form the particles.

DETAILED DESCRIPTION OF PREFERRED EMBODIMENTS

Introduction to Invention

Figure 1:
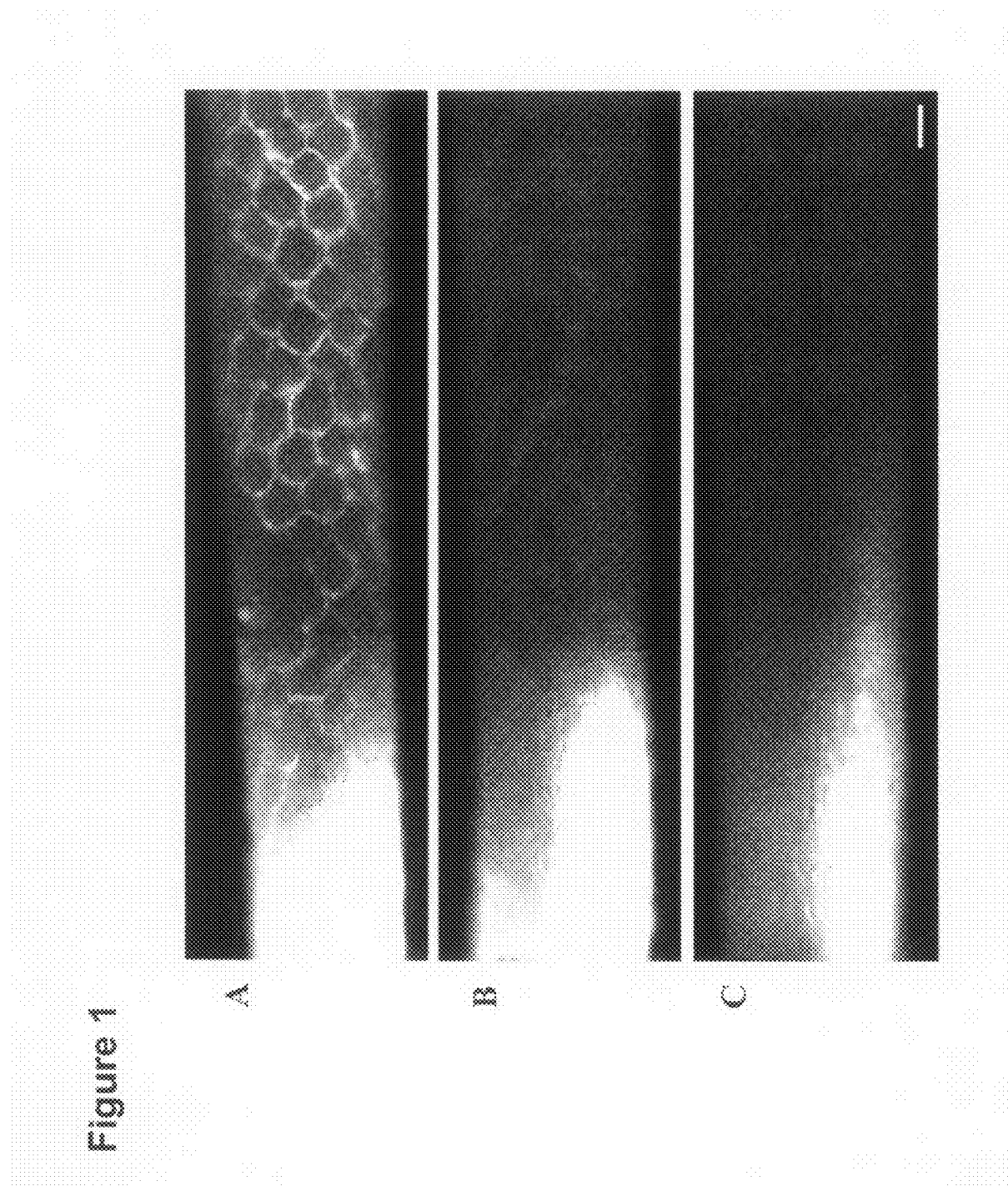
FIG. 1 is a photomicrographic montage showing a comparison of nanoparticle uptake into the initial lymphatics. It depicts fluorescence microlymphangiography of the lymphatic capillary network in mouse tail skin after 90 min infusion with fluorescence-loaded PPS nanoparticles of (A) 20, (B) 45 and (C) 100 nm diameter. Images were taken at constant exposure. The hexagonal lymphatic network was clearly visible with the 20 nm particles. Bar=100 µm.

Nanoparticles with suitable properties can be used to specifically target therapeutic substances to antigen-presenting cells (APCs) including dendritic cells (DCs) in lymph nodes. The effects of nanoparticle size on lymphatic uptake, lymph node retention, and internalization by lymph node APCs and DCs are demonstrated herein in response to intradermal injections in mice (which have similar size lymphatic capillaries as those in humans—10-80 μm—although these are highly variable in both species [20, 42]). While a variety of nanoparticle sizes may be used, nanoparticles of about 20 nm diameter are most readily taken up and, further, are retained in the lymph nodes for longer times (up to 120 h) than has been previously reported for other particles [31-34, 36]. Certain nanoparticle surface chemistries are surprisingly demonstrated to activate complement. Within the lymph node, it was shown that the complement-activating nanoparticles are internalized effectively by resident APCs (MHCII$^+$ cells which include DCs and some macrophages) and other nonantigen presenting macrophages (Nano without a targeting ligand. A large fraction (up to 50%) of lymph node resident DCs internalized the 20 nm complement-activating nanoparticles, with the number increasing over time. It was found that DC maturation occurred following complement-activating nanoparticle internalization.

Size and surface chemistry are simultaneously important: complement activating nanoparticles that are not sized to enter lymphatics at a given efficiency (e.g., PLURONIC-stabilized 100 nm nanoparticles) are not as powerful an adjuvant as relatively smaller nanoparticles (e.g., 25 nm) of the same chemistry that have a higher efficiency of entry. Complement non-activating nanoparticles that are sized to readily enter the lymphatics (e.g., 25 nm PPS nanoparticles stabilized with methoxy-terminated PLURONIC) are not as powerful an adjuvant as the same sized nanoparticles of a surface chemistry that does activate complement (e.g., PLURONIC stabilized 25 nm PPS nanoparticles). That complement activation plays a key role in the mechanism is evidenced by poor immune response in C3−/− animals injected with antigen-coupled 25 nm PLURONIC-stabilized PPS nanoparticles. Small (e.g., 20-45 nm) hydroxylated nanoparticles (e.g., PLURONIC-stabilized PPS nanoparticles) thus offer a strategy to deliver immunotherapeutic agents to DCs and other APCs in lymph nodes.

Certain surface chemistries can be utilized to activate APCs, including DCs and then induce T cell dependant adaptive immune responses. Some material surfaces can activate the complement cascade, including hydroxylated surfaces [117] or hydroxylated surfaces obtained by stabilization with PLURONIC [118]. Materials surfaces can be conjugated to certain hydroxylated molecules and biomolecules to activate complement. For instance, artisans may apply techniques set forth herein to accomplish the conjugation. Moreover, implants, medical devices, or other carriers besides nanoparticles may receive a layer of complement-activating polymer as described herein, or the polymers or the hydroxyls can be introduced directly onto such materials. In adjuvant development, the conventional approach utilized by scientists to activate cells, such as, DCs through activators of the Toll-like receptors, such as lipopolysaccharide (LPS). [119-121]. But it has been discovered that certain nanoparticle surface chemistries can activate a different aspect of innate immunity, namely the complement cascade: the detailed examples herein demonstrate that hydroxylated nanoparticles, such as those obtained by stabilization with PLURONIC, can activate complement and that this can in turn activate APCs including DCs and induce T cell dependant humoral and cellular immunity. In other work on nanoparticles as adjuvants, not employing a complement mechanism, polymer nanoparticle size determined the extent to which DCs were targeted and activated: with carboxylated polystyrene nanoparticles, intermediate (45 nm) sized nanoparticles are taken up by DCs and activate them, but smaller ones (20 nm) do not [116]. With nanoparticles described herein, however, complement can be activated and this provides a powerful signal for activation of DCs and induction of T cell dependant humoral and cellular aspects of the adaptive immune response.

Complement activation is known to enhance the adaptive immune response, specifically B cell immunity. Previous work has demonstrated that complement proteins C3b and C3d can be utilized as a molecular adjuvant for enhancement of B cell-dependant humoral immunity. Immunization of mice with a fusion of C3b or C3d to model antigens demonstrates a significant increase in the acquired immune B cell response compared to free antigen alone [134, 135]. The mechanism that C3b and C3d adjuvants work may be through direct binding of the C3d receptor (CD21/35) which associates with CD19, a known amplifier of B cell activation. However, CD21/35 has been found to not always be necessary for this B cell response [136]. One certainty to C3b- and C3d-antigen fusions is that their adjuvant capacity for humoral immunity is through direct interaction with B cells [137]. This is different than T cell-dependant humoral immunity, which occurs when antigen is uptaken by DCs as taught herein, DCs mature, DCs process and present antigen through MHC II to CD4 T cells, CD4 T cells present antigen to B cells, and finally B cells produce antibodies. While complement has been discovered to be involved in T cell-dependant immunity, the mechanisms by which this occurs have not been described [138]. Moreover, it has not been previously suggested that complement activation could be used as a molecular adjuvant for T cell dependant immunity.

The systems herein, however, describe how complement activation can be used as a molecular adjuvant for T cell dependant immunity. Moreover, some embodiments include nanoparticles that activate complement through nanoparticle surface chemistries. Specifically, for instance, the results show that 25 nm PLURONIC-stabilized complement-activating PPS nanoparticles induce DC maturation and demonstrate for the first time that complement activation through hydroxylated surfaces can be utilized as a danger signal to induce DC maturation. Also as described herein, for the first time complement-activation through PLURONIC-stabilized nanoparticles is used as an adjuvant for the induction of DC-mediated T cell-dependant humoral and cellular immunity.

Immune System Targeting

Antigen-presenting cells (APCs) are highly efficient phagocytic cells that utilize MHC class I, II and other co-stimulatory molecules (i.e., CD86 and CD80) to stimulate naïve T cells and induce cell-mediated immunity. APCs, which include some macrophages and the more potent dendritic cells (DCs), are present in peripheral tissues where they act as sentinels that, following internalization and processing of foreign antigens, subsequently undergo maturation and migration to lymph nodes for the purpose of antigen presentation to T cells [1-3]. With the critical roles that APCs and DCs play in adaptive immunity, various experiments are being made to target these cells with immunomodulating agents, such as DNA, proteins, and polypeptides [4-14]. Polypeptide is a term that refers to two or more amino acids joined together, and includes proteins.

Polymer- and liposome-based delivery systems have focused primarily on delivery of protein and DNA to peripheral DCs, where they first internalize the drug vehicles and then migrate to lymph nodes within ~1-2 days to activate T cells [9, 12, 13]. Until recently, it was not clear whether immature DCs, capable of taking up antigens, were present in lymph nodes. However, recent studies have established that a substantial fraction of resident DCs in the lymph nodes are phenotypically immature and capable of internalizing antigens and particles there [15, 16]. Thus, as explained herein, resident lymph node APCs may also be utilized as targets for immunotherapeutic drugs or other therapeutic agents. A potential benefit of targeting lymph node APCs or DCs instead of those in peripheral sites is that premature antigen presentation (i.e., a migrating DC that expresses antigen on its surface prior to reaching a lymph node) can often lead to immune cell tolerance [13, 17, 18]; therefore, delivery to lymph node APCs may potentially avert this problem. Additionally, other DC targeting studies use conjugated targeting ligands such as anti-Dec-205 and anti-CD11c to increase DC specificity [4, 5, 8, 9, 12, 19].

What has not been conventionally appreciated, however, is that one can effectively exploit the fact that DCs are by nature highly phagocytic and present in lymph nodes at high concentrations. Accordingly, materials and methods to specifically target these cells in lymph nodes have been developed, as explained herein, including targeting without the use of a targeting ligand. A targeting ligand refers to a chemical group that specifically binds to a particular chemical group on a cell, e.g., a cell surface receptor or a cell surface protein. Thus some embodiments can be targeted based on the size and other physical properties and are targeted with no exogenous polypeptide, with no exogenous ligand, with no exogenous nucleic acid, with no antibody or fragment thereof, or with no exogenous ligand for any of a receptor, cell surface molecule, extracellular matrix molecule, cell surface antigen, cell marker molecule, or polysaccharide.

In order to target APCs, including DCs, in lymph nodes, it is useful, as demonstrated herein, to design delivery vehicles that can be readily taken up into lymphatic vessels and retained in draining lymph nodes. A delivery vehicle refers to an agent, e.g., a particle that delivers a therapeutic agent, e.g., an antigen or immunosuppressant drug. A primary role of the lymphatic system is the uptake of fluid and particulates from the interstitial space as a small but important component of the microcirculation [20-23].

Other in vivo lymphatic targeting experimental studies using liposomes and polymer particles to investigate the lymphatic system have indicated that particle size can be a factor for lymphatic uptake from the interstitial space [21, 24-29]. Liposomes larger than 170 nm generally showed poor lymphatic uptake and remained at the injection site, whereas particles in the range of 40-70 nm showed significant uptake into lymphatic vessels [25].

One such study using carboxylated polystyrene particles teaches that particles only in the narrow range of 40-50 nm are practically useful because this size is a danger signal recognized by DCs; consequently, DCs are activated in dermal sites and not in lymph nodes [116]. This polystyrene bead study showed that beads accumulate in lymph nodes at intermediate sizes (40 nm) more than smaller (20 nm) and larger (>100 nm) sizes and taught that 40-50 nm was the size that should be used for beads. More specifically, this study showed that very small particles (20 nm) and larger particles (100 nm) were found to accumulate significantly less than 40 nm particles in cells that were positive for DC markers, as indicated by the DC antigen DEC205 [116]. The authors teach that 40 nm polystyrene beads cause activation and migration of DCs in dermal sites to lymph nodes; therefore 40 nm beads could not be targeting lymph node resident DCs.

Further, the polystyrene bead study teaches that bead size is a danger signal for DCs because DCs have evolved to recognize viral size ranges. The bead size, therefore, would control successful DC targeting, with correctly sized beads being recognized by DCs in the periphery, and causing activation of the DCs. This teaching is in sharp contrast to the successful use of smaller nanoparticles for DC activation (less than about 40 or about 35 or about 25 nm) as described herein. This teaching is also in contrast to the results herein showing that surface chemistry is a danger signal, e.g., as in PLURONIC-stabilized PPS nanoparticles which utilize hydroxyl surface chemistry to activate complement as a danger signal. Moreover results herein relate particle size to lymph node targeting capability and not DC size recognition. For instance, the, 25 nm PLURONIC-stabilized complement-activating nanoparticles were better than 100 nm PLURONIC-stabilized complement-activating nanoparticles at activating DCs and adaptive T cell immunity after in vivo injection.

The carboxylated polystyrene beads were used as an experimental model system at least in part because their convenient synthesis and emulsion polymerization characteristics give rise to a narrow and controllable size distribution [116]. Potential disadvantages for use as a therapeutic or prophylactic system are associated with the polystyrene beads. For, example, no biological pathway exists by which such particles may be degraded and eliminated from the body. In contrast, a biodegradable system as described herein will degrade readily and effectively to soluble polymer in response to an in vivo environment, e.g., as in PPS nanoparticles that degrade under oxidative conditions encountered after endocytosis and processing. While degradation of the nanoparticles may be beneficial, it is not necessarily a requirement for use as an adjuvant.

Interactions between the particle surface and the interstitium may be another factor that plays a role in lymphatic uptake [30]. Steric stabilization by coating liposomes and particles with hydrophilic layers such as poly(ethylene glycol) (PEG) and its copolymers such as PLURONICS (including copolymers of poly(ethylene glycol)-bl-poly(propylene glycol)-bl-poly(ethylene glycol)) may reduce the non-specific interactions with proteins of the interstitium as demonstrated by improved lymphatic uptake following subcutaneous injections [21, 27, 31-35]. All of these facts point to the significance of the physical properties of the particles in terms of lymphatic uptake.

However, while smaller particles are taken up more readily, they also pass out of the lymph node more easily; achieving both efficient lymphatic uptake and lymph node retention is thus significant. Accordingly, certain nanoparticle embodiments have features that address both uptake and retention, as is evident from the examples and embodiments set forth herein. With respect to the size of nanoparticles, for example, investigations of the lymphatic system indicated that only 1-2% of injected 70 nm liposomes are retained in the lymph nodes beyond 12 h post-injection [30], and that node retention of large liposomes (>70 nm) is more efficient than that of smaller liposomes [24, 29]. This apparently is due in part to the fact that lymph node macrophages phagocytose larger particles more efficiently. While it is conventionally assumed that coating of liposomes with steric protectants such as PEG should reduce phagocytosis by macrophages, it has been shown that such coating does not significantly affect lymph node retention [36]. It has also been conventionally assumed that particles phagocytosed in the lymph nodes are done so primarily by macrophages [21, 27, 29, 30, 32, 36, 37]. With carboxylated polystyrene nanoparticles, it was found that 20 nm nanoparticles were taken up much less by DCs than were 40 nm nanoparticles in vivo [116]. Therefore, besides delivering drugs for uptake by macrophages, it is advantageous to deliver drugs to lymph nodes for uptake by other APCs, including DCs. As shown below, certain embodiments of the particles of this invention are, in fact, taken up by APCs and/or DCs even at small sizes at least as low as 20 nm.

Previous studies have suggested that following antigen uptake, powerful biological "danger signals" such as inflammatory cytokines (i.e. CD40 ligand) are necessary to mature DCs and subsequently induce cell-mediated immunity [5, 12, 38]. However it may be advantageous to forego such signals. In fact, in some embodiments, it is the nanoparticles themselves are used as a maturation stimulus that avoids the use of conventional biological "danger signals", e.g., some polypeptides, antibodies, nucleic acid sequences. These results are evident in the maturation response of DCs that was observed following nanoparticle internalization in vivo.

Nanoparticle Formulations

As documented herein, size is related to nanoparticle uptake and retention in lymph nodes. Nanoparticle lymphatic uptake, lymph node retention, and localization within lymph nodes and among cell populations there are documented herein. One challenge using conventional approaches is obtaining both efficient lymphatic uptake and lymph node retention, since nanoparticle properties, such as size and surface characteristics, can have conflicting effects. In general, smaller particles have better lymphatic uptake than larger particles but lower lymph node retention. Nanoparticles with a size of about 5 nm to about 100 nm diameter are preferred; artisans will immediately appreciate that all the ranges and values within the explicitly stated ranges are contemplated, e.g., 20, 25, 30, 35, 40, 45, 50, 55, 60, 65, 70, 75, or 80 nm. The nanoparticles may be made in a collection that of particles that has a mean diameter from about 5 to about 100 nm; artisans will immediately appreciate that all the ranges and values within the explicitly stated ranges are contemplated, e.g., from about 10 to about 70 nm. The size distribution of such a collection of particles can be controlled so that a coefficient of variation (standard deviation divided by mean particle size) around a mean diameter of a collection of the particles may be less than about 50, about 35, about 20, about 10, or about 5 nm. [39]; artisans will immediately appreciate that all the ranges and values within the explicitly stated ranges are contemplated.

Physical properties are also related to a nanoparticle's usefulness after uptake and retention in lymph nodes. These include mechanical properties such as rigidity or rubberiness. Some embodiments are based on a rubbery core, e.g., a poly (propylene sulfide) (PPS) core with an overlayer, e.g., a hydrophilic overlayer, as in PEG, as in the PPS-PEG system recently developed and characterized for systemic (but not targeted or immune) delivery [39, 40]. The rubbery core is in contrast to a substantially rigid core as in a polystyrene or metal nanoparticle system. The term rubbery refers to certain resilient materials besides natural or synthetic rubbers, with rubbery being a term familiar to those in the polymer arts. For example, cross-linked PPS can be used to form a hydrophobic rubbery core. PPS is a polymer that degrades under oxidative conditions to polysulfoxide and finally polysulfone [41], thus transitioning from a hydrophobic rubber to a hydrophilic, water-soluble polymer [39]. Other sulfide polymers may be adapted for use, with the term sulfide polymer referring to a polymer with a sulfur in the backbone of the mer. Other rubbery polymers that may be used are polyesters with glass transition temperature under hydrated conditions that is less than about 37° C. A hydrophobic core can be advantageously used with a hydrophilic overlayer since the core and overlayer will tend not to mingle, so that the overlayer tends to sterically expand away from the core. A core refers to a particle that has a layer on it. A layer refers to a material covering at least a portion of the core. A layer may be adsorbed or covalently bound. A particle or core may be solid or hollow. Rubbery hydrophobic cores are advantageous over rigid hydrophobic cores, such as crystalline or glassy (as in the case of polystyrene) cores, in that higher loadings of hydrophobic drugs can be carried by the particles with the rubbery hydrophobic cores.

Another physical property is the surface's hydrophilicity. A hydrophilic material has a solubility in water of at least 1 gram per liter when it is uncrosslinked. Steric stabilization of particles with hydrophilic polymers can improve uptake from the interstitium by reducing non-specific interactions; however, the particles' increased stealth nature can also reduce internalization by phagocytic cells in lymph nodes. The challenge of balancing these competing features has been met, however, and this application documents the creation of nanoparticles for effective lymphatic delivery to DCs and other APCs in lymph nodes. Thus some embodiments include a hydrophilic component, e.g., a layer of hydrophilic material. Examples of suitable hydrophilic materials are one or more of polyalkylene oxides, polyethylene oxides, polysaccharides, polyacrylic acids, and polyethers. The molecular weight of polymers in a layer can be adjusted to provide a useful degree of steric hindrance in vivo, e.g., from about 1,000 to about 100,000 or even more; artisans will immediately appreciate that all the ranges and values within the explicitly stated ranges are contemplated, e.g., between 10,000 and 50,000. The examples include a particle with a hydrophilic surface that is a PEG derived from a PLURONIC that was used as a stabilizer during synthesis as an emulsion.

The nanoparticles may incorporate functional groups for further reaction. Functional groups for further reaction include electrophiles or nucleophiles; these are convenient for reacting with other molecules. Examples of nucleophiles are primary amines, thiols, and hydroxyls. Examples of electrophiles are succinimidyl esters, aldehydes, isocyanates, and maleimides. For instance, using PPS-PLURONIC nanoparticles as an example, particles are then synthesized as described in Example 1 with the difference that 2% of the PLURONIC is replaced with OVA/OVA$_{257-264}$/OVA$_{323-339}$ derivatized PLURONIC. A total amount of 1.5% PLURONIC is used. Reaction time is reduced to 2 h and base is added at 1:1 equimolar ratio to initiator-thiols in order to reduce the exposure of the protein or peptides to basic conditions during nanoparticle synthesis. This scheme is only one exemplary method for PEG functionalization; several other approaches can be utilized depending on the protein or peptide being conjugated [111].

The nanoparticles may also incorporate functional groups or motifs for complement activation. A preferred functional group is hydroxyl, which is particularly effective for activating complement as documented herein. Other functional groups that are nucleophilic can react with the thioester in C3. It is demonstrated herein that hydroxylated nanoparticle surfaces are particularly useful in targeting APCs, including DCs, in the lymph node. In the case of the PPS nanoparticles of the examples herein, hydroxylation was obtained by stabilization with PLURONIC terminated with hydroxyl groups. When these hydroxyl groups were converted to methoxy groups to block the hydroxy group, the nanoparticles did not function well as adjuvants. When the hydroxylated nanoparticles were tested in C3−/− mice, their adjuvant effect was vastly diminished. These results, combined with measurements described in the examples herein of C3 activation, demonstrate the particular usefulness of targeting APCs, including DCs, with complement-activating nanoparticles. Accordingly, in some embodiments, nanoparticles rely only on OH to activate complement and exclude one or more of: cations at pH 7.0-7.4, amines, primary amines, secondary amines, anions at pH 7.0-7.4, thiols, zwitterions at pH 7.0-7.4; alternatively such groups are present on the nanoparticle but it is a layer of polymer on the nanoparticle that excludes one or more of such groups. Alternatively, the nanoparticle and/or layer has no group effectively capable of forming an ion at pH 7.0 to 7.4 except OH.

Functional groups can be located on the particle as needed for availability. One location can be as side groups or termini on the core polymer or polymers that are layers on a core or polymers otherwise tethered to the particle. For instance, examples are included herein that describe PEG stabilizing the nanoparticles that can be readily functionalized for specific cell targeting or protein and peptide drug delivery.

Biodegradable polymers may be used to make all or some of the polymers and/or particles and/or layers. Biodegradable refers to polymers that are subject to degradation by spontaneous hydrolysis, chemical attack by enzymes that cleave specific amino acid sequences, or by incorporating functional groups that are oxidation-sensitive. Polymers subject to spontaneous hydrolysis will degrade in vitro in aqueous solution kept at a pH of 7.0 to 7.4 as a result of functional groups reacting with the water in the solution. The term "degradation" as used herein refers to becoming soluble, either by reduction of molecular weight (as in the case of a polyester) or by conversion of hydrophobic groups to hydrophilic groups (as in the case of PPS). Polymers with ester groups are generally subject to spontaneous hydrolysis, e.g., polylactides and polyglycolides. Many peptide sequences subject to specific enzymatic attack are known, e.g., as degraded by collagenases or metalloproteinases: sequences that are degraded merely by biological free radical mechanisms are not specifically degraded. Polymers with functional groups that are oxidation-sensitive will be chemically altered by mild oxidizing agents, with a test for the same being enhanced solubilization by exposure to 10% hydrogen peroxide for 20 h in vitro. For example, PPS is an oxidation-sensitive polymer [39].

While PPS particles were used as an exemplary system to demonstrate how to make and use the nanoparticles, alternative materials may be used. In general, the features for each component of the particle system may be freely mixed-and-matched as guided by the need to make a functional particle. For instance, other particles that are small (e.g., less than about 100 nm or less than about 70 nm) and thus enter the lymphatic circulation efficiently may be used. Such particles may optionally be grafted with an overlayer of PEG, or otherwise incorporate a hydrophilic polymer, and may optionally be grafted with antigen, danger signals, or both. For example, a PEG-containing block copolymer can be adsorbed to a degradable polymer nanoparticle of appropriate size, and antigen can be further attached to the surface of such a treated polymer. As another example, a PEG-containing block copolymer can be adsorbed to an inorganic nanoparticle of appropriate size, and antigen can be further attached to the surface of such a treated polymer. While degradation of the nanoparticle core may be desirable, it is not necessarily required.

Micellar systems may also display the same useful characteristics as described above, including micelles formed from AB and ABA block copolymers of poly(ethylene glycol) and PPS [100-104]. When such copolymers are formed with a molecular fraction of poly(ethylene glycol) that is relatively high, e.g., in excess of approx. 40%, then spherical micelles can be expected to form under certain conditions. These micelles can be small, e.g., meeting the size mentioned above for lymphatic entry, and may optionally be grafted with an overlayer of PEG, or otherwise incorporate PEG or other polymers to achieve similar properties. Moreover, they can be conjugated with antigen, as taught herein, danger signals or both at the micelle surface. The block copolymer can terminate in a hydroxyl group, for complement activation, and it is particularly beneficial to have the hydrophilic block terminate in a hydroxyl group, so that this hydroxyl group will be more readily available on the micellar nanoparticle surface for complement binding. Such hydroxylated such surfaces can be tailored to effectively activate complement. A particularly useful hydrophilic block is PEG, terminated in a hydroxyl group. In addition to micelle-forming polymer architectures, block sizes and block size ratios can be selected to form vesicular structures. There also exists a number of other possible chemical compositions of micellar formulations that may be used [105-108].

Some polymer systems are themselves nanoparticulate and are included in the term nanoparticle. For example, dendrimers are a class of polymer that can be nanoparticulate in the nm range [141]. These polymers comprise a high number of functional groups at their surface, for example which have been used to conjugate to biomolecules and other groups [142, 143]. Analogously, antigen could be conjugated to the dendrimer surface. Moreover, the functional groups on the dendrimer surface could be optimized for complement activation, for example by hydroxylation. Some dendrimer-DNA complexes have been demonstrated to activate complement [144, 145]. Thus, dendrimers represent an interesting nanoparticulate chemistry that could be adapted for lymphatic targeting using the techniques described herein, for antigen conjugation, and for complement activation, e.g., as in U.S. Pat. Pub. Nos. 2004/0086479, 2006/0204443, and in U.S. Pat. Nos. 6,455,071 and 6,998,115, which are hereby incorporated by reference herein to the extent they do not contradict what is explicitly disclosed.

On the other hand, dendrimers have a shape that is highly dependent on the solubility of its component polymers in a given environment, and can change dramatically according to the solvent or solutes around it, e.g., changes in temperature, pH, ion content, or after uptake by a DC. In contrast, nanoparticles that have physical dimensions that are relatively more stable than dendrimers or other merely branched polymer systems can be useful for storage purposes or as related to or biological activity, e.g., a solid core with a hydrophilic corona will consistently present the corona to its environment. Accordingly, some embodiments of nanoparticles rely on particles that are not dendrimers, or that have a core that is a solid and/or have a core that is a cross-linked hydrogel. A PPS-based nanoparticle is not a dendrimer and has a solid core.

Immunotherapy with Nanoparticles

In use, such nanoparticles are useful as, e.g., antigen and drug delivery vehicles to target APCs, specifically DCs, in lymph nodes. The ability to deliver antigen and/or drugs and/or danger signals to DCs in lymph nodes is a useful approach to immunotherapy. The ability to target lymph node DCs and other APCs effectively with nanoparticles provides a method for delivery of antigenic proteins and polypeptides and antigen-encoding nucleic acids. Since DCs are critically involved in initiating cell-mediated immunity by antigen presentation to T cells, this delivery approach can be utilized for several vaccine and immunotherapy applications. Further, the nanoparticles are useful as diagnostic tools (e.g., imaging), research tools (e.g., as sold in ALDRICH catalogs or for visualization using microscopes), or in vitro drug delivery or visualization (e.g., APC and/or DC and/or macrophage uptake in vitro of drugs or imaging agents).

The antigen and/or drugs and/or danger signals may be covalently attached to the particles, adsorbed to the particles, loaded into the particles, or mixed with a collection of the particles for contemporaneous introduction into a patient. Motifs for covalent bonding are discussed elsewhere herein, and may be applied in this instance also. Adsorption can be accomplished by mixing the agent and the particles for a predetermined amount of time and then physically separating the particles from the mixture, e.g., by centrifugation or filtration. The separation may take place before or after administration, in vitro or in the body, e.g., by injecting the mixture and allowing diffusive and convective forces to separate the components. Loading may be performed during or after particle synthesis. For instance, the particles may be polymerized in the presence of the agent, which will become entrapped, either by adsorption or by phases separation as in a micellar-based polymerization. Loading after synthesis may be accomplished as needed, e.g., by exposing the particles to an agent in a first solvent that swells the particles or permits ready diffusion of the agent and then exposing the particles to a second solvent that contracts the particles or restores them to an aqueous solution that stops or slows diffusion of the agent, for instance: loading a hydrophobic drug in organic solvent and storing the particles in aqueous solution. Mixing for contemporaneous introduction may be accomplished by, e.g., introducing the particles into a syringe having a solution of antigen and/or drugs and/or danger signals and coinjecting them into a patient.

Immunotherapy with Nanoparticles and Immunosuppressive Drugs

Immunosuppression is a critical form of immunotherapy that is greatly needed in situations of clinical transplantation (e.g., allografts) and autoimmune diseases (e.g., multiple sclerosis). The use of immunosuppressive drugs such as corticosteroids (e.g., Cyclosporin A) and rapamycin has led to great advances in the treatment of these immune disorders [122]. T cells are generally considered to be important targets of immunosuppressive drugs, which act by inhibiting genes for inflammatory cytokines, primarily IL-2 and TNF-$\gamma$, and therefore reduce T cell proliferation. Another approach for immunosuppresion being developed is the use of antibodies to block the T cell receptors CD28 and CD40 [123]. Blocking these receptors leads to insufficient activation by co-stimulatory molecules located on DCs and therefore causes a tolerance effect that effectively aborts T cell proliferation. However treatment with corticosteroids or blocking antibodies is very non-specific and may lead to side effects such as reducing the ability of the immune system to fight off other infections. Therefore a strategy for more specific immunosuppression, one that induces antigen-specific tolerance would be an exceptional advance in immunotherapy.

Recently it has been discovered that DCs may be a target for immunosuppression; in addition to their ability to stimulate T cell immunity, DCs are also capable of regulating T cell tolerance [124]. Dexamethasone (Dex) is a synthetic glucocorticoid utilized for immunosupresion in applications such as preventing rejection of allograft transplants. Traditionally it has been thought that glucocorticoids act solely on T cells. However recent studies have demonstrated that Dex can act on DCs to down regulate the expression of the co-stimulatory molecules and the secretion of inflammatory cytokines [125, 126]. This has substantial implications for the potential to utilize DCs for the induction of tolerance. A DC that presents antigen to T cells in the absence of co-stimulatory molecules will induce T cell anergy or tolerance to the presented antigen.

Immunosuppressive drugs may be delivered with the nanoparticles. In some embodiments, antigen can be effectively targeted to the lymph node DCs by virtue of their size and interaction with interstitial flows and entry into the lymphatics. Delivery of an antigen and at the same time as immunosuppressants to prevent DC activation would lead to tolerance. In such cases, nanoparticles that do not activate complement may be beneficial. Some of the major immunosuppressive drugs are glucocorticoids, which are hydrophobic and can be loaded into the hydrophobic PPS core of the nanoparticles. Certain glucorticoids such as Dexamethasone, tacrolimus, and Cyclosporin A have demonstrated that they inhibit the maturation and allostimulatory capacity of DCs by downregulating the expression of co-stimulatory molecules (i.e., CD80 and CD86) and secretion of inflammatory cytokines (i.e., IL-6 and TNF-$\alpha$) [125-131].

Immunosuppressive drugs may be loaded into nanoparticles described herein and introduced into a patient. The nanoparticles may be specifically targeted to the lymphatic system, and the lymph nodes, and may be specifically targeted for uptake by APCs and/or DCs. Hydrophobic drugs or other agents may advantageously be delivered using nanoparticles with a hydrophobic components or cores. Further, an antigen may be delivered in combination with a drug. The antigen may be associated with a nanoparticle, e.g., by coinjection, adsorption, or covalent bonding.

For example, one strategy is to load hydrophobic immunosuppressive drugs (e.g., Dex) into the core of nanoparticles stabilized with methoxy-terminated PLURONIC (thus not hydroxylated and not complement activating) PPS nanoparticles and graft antigen to the surface. Therefore by delivering Dex or other immunosuppressive drugs along with antigen to DCs in lymph nodes, it is possible to down-regulate co-stimulatory molecules but still deliver antigen and in turn cause antigen-specific tolerance. Therefore nanoparticles, e.g., PPS nanoparticles stabilized with methoxy-terminated PLURONIC, with the combination of antigen conjugation and immunosuppressive drug loading, may be utilized to induce tolerance for applications such as therapy for autoimmune diseases and transplant rejections.

Immunotherapy with Nanoparticles and Antigens

APCs that internalize protein antigens can process and present the antigenic peptide epitope through MHC-I and II pathways. One immunotherapeutic approach involves covalently attaching one or more antigens to a nanoparticle, or otherwise associating them. Antigens are polypeptides without or with glycosylation that can be recognized by an immune system, and are generally at least about three amino acids in length. Antigens can also be encoded via nucleic acid sequences such as DNA or RNA. For example, DNA can be encode an antigen if it encodes a polypeptide antigen present on pathogens. Following delivery of the DNA to nuclei of APCs, expression of the antigenic polypeptide antigen would occur and presentation of it on MHC I. Whole proteins can be used, but antigenic fragments can be used, so that polypeptides having between about 3 to about 20 residues can be used; artisans will immediately appreciate that all the ranges and values within the explicitly stated ranges are contemplated, e.g. less than about 10 residues. Since nanoparticles may be used that directly activate the complement system without involving a polypeptide, antigens that do not activate the complement system may be used.

Antigens can be used for immunotherapy against many different diseases. One specific application is for tumor immunotherapy. Useful antigens are displayed on tumor cells but not healthy cells. Several antigens have been identified as specific to certain types of tumors, such as Caspase-8, MAGE-1, Tyrosinase, HER-2/neu, and MUC-1 [112]. With this in mind, nanoparticles can be used to deliver such antigens to DCs in lymph nodes as a means for activating T cells to attack tumors. Another application is prophylaxis for infectious diseases. Exposure to antigens can create resistance against such diseases or act as a vaccination for various conditions.

Immunotherapy with Nanoparticles and Nucleic Acids

Some nanoparticle collections may include nanoparticles and nucleic acids, e.g., DNA or RNA that encode an antigen. Moreover, these may also include an expression cassette, include a promoter or enhancer, be part of a vector, or otherwise incorporate gene delivery motifs as are known in these arts, see, e.g., U.S. Pat. Nos. 7,160,695, 7,157,089, 7,122, 354, 7,052,694, 7,026,162, 6,869,935, which are hereby incorporated by reference to the extent they do not contradict what is explicitly disclosed herein. Moreover, the sequences may encode other therapeutic biomolecules Nucleic acids antigens such as DNA can attached to nanoparticles (e.g., the surface of Pluronic-stabilized PPS nanoparticles) as described for antigens and other agents herein. And, for instance, DNA-polymer conjugation can be performed through electrostatic adsorption, polymer-biotinylation [139]. A number of other chemical conjugation strategies exist to attach polymers to DNA, which may be adapted for use herein [140]. By using the nanoparticles described herein, APCs including lymph node DCs may be targeted for antigen gene expression as well as activated to ensure appropriate T cell stimulation.

Antigen Conjugation

A variety of schemes for attaching antigens to nucleophilic or electrophilic functional groups are available. In general, such schemes can be adapted to the attachment of drugs or danger signals, as appropriate.

By way of example, the attachment of antigens to PLURONIC in the PPS nanoparticles of the examples is provided. Antigen conjugation to PPS nanoparticles can be accomplished by functionalizing PLURONIC (a block co-polymer of PEG and PPG) surface with proteins or peptides. Pluronic F127 (Sigma), divinylsulfone (Fluka), sodium hydride (Aldrich), toluene (VWR), acetic acid (Fluka), diethylether (Fisher), dichloromethane (Fisher) and Celite (Macherey Nagel) were used as received. The reaction was carried under argon (Messer). $^1$H NMR was measured in deuterated chloroform (Armar) and chemical shifts ($\delta$) are given in ppm relative to internal standard tetramethylsilane (Armar) signal at 0.0 ppm. A solution of 15 g (1.18 mmol) of Pluronic F-127 in 400 ml toluene was dried by azeotropic distillation for 4 h using a Dean-Stark trap. The solution was cooled in an ice bath and 0.283 g (11.8 mmol) sodium hydride was added. The reaction mixture was stirred for 15 min and 3.55 ml (35.4 mmol) divinyl sulfone (Sigma-Aldrich) was added quickly. After stirring in the dark for 5 days at room temperature the reaction was quenched by adding 1.35 ml (23.6 mmol) acetic acid. After filtering over celite and concentrating the filtrate under reduced pressure to a small volume the product was precipitated in 1 liter of ice-cold diethylether. The solid was filtered off, dissolved in minimum amount of dichloromethane and precipitated in ice-cold diethylether four times in total. The polymer was dried under vacuum to yield 6.0 g and stored under argon at −20° C. prior to OVA conjugation. NMR showed the presence of vinyl sulfone and the degree of functionalization was 88%. $\delta$=1.1 (m, $CH_3$, PPG), 3.4 (m, CH, PPG), 3.5 (m, $CH_2$, PPG), 3.6 (PEG), 6.1 (d, $CH_{cis}$=CH—$SO_2$) and 6.4 (d, $CH_{trans}$=CH—$SO_2$), 6.85 (dd, $CH_2$=$CHSO_2$—).

Peptide or protein antigens can then be conjugated to PLURONIC vinylsulfone (VS). A model protein for investigating DC antigen presentation is ovalbumin (OVA). OVA possesses the antigenic peptides $OVA_{257-264}$ and $OVA_{323-339}$ which are processed by DC through MHCl and II pathways, respectively. $OVA_{257-264}$ and $OVA_{323-339}$ are conjugated to cysteine residues through the use of a peptide synthesizer. The peptides are then conjugated to PLURONIC-VS by reaction with its cysteine thiols. 18 mg of peptide is solubilized in 6.43 ml 0.1 M sodium phosphate buffer at pH 8.5 to yield a 2 mM solution. 60 mg (1.68 mM) PLURONIC-VS are added. The mixture is stirred during 3 h and aliquots for thiol detection by Ellman's are taken every 15-30 min. 4 mg of Ellman's reagent (5,5' dithio-bis-(2-nitrobenzoic acid)) are solubilized in 1 ml of 0.1 M sodium phosphate and 1 mM EDTA (to chelate divalent metal ions, which can oxidize sulfhydryls) at pH 8.5. 15 µl is mixed with 1.5 ml 0.1 M sodium phosphate and 30 µl of the reaction mixture quenched with 120 µl of sodium phosphate at pH 7. Following mixing and incubating at room temperature for 15 min, the absorbance is measured at 412 nm. The quantity of thiols is calculated as: c=Abs/E*D, with E (Extinction factor)=14150 $M^{-1}$ and D being a dilution factor. The PLURONIC was dialyzed against water through a membrane of 6-8 kDa MWCO and the solution is freeze dried. The yield is ~88% with full conversion of the vinyl sulfone groups as confirmed to $^1$H-NMR. Conjugation of OVA to PLURONIC-VS is performed by a similar strategy by utilizing free cysteine thiols and lysine amines [109-111]. The PL-VS-OVA peptide/protein is then stored at −20° C. until used for nanoparticle synthesis.

Antigen may be conjugated to the nanoparticles by other means including covalent conjugation to amino acids that are exogenous to the naturally occurring polypeptide antigen, covalent conjugation to amino acids that are endogenous to the naturally occurring antigen, physiochemical adsorption, and other means.

Immunotherapy with Nanoparticles and Danger Signals

Another immunotherapy approach involves the application of danger signals. The results herein show that PLURONIC-stabilized complement-activating (and thus hydroxylated) PPS nanoparticles provide the function of a danger signal or stimulus that matures DCs as evidenced by the increase in the expression of the co-stimulatory molecules CD86 and CD80. While the nanoparticles do not require a non-complement danger signal or maturation signal, in some cases adding such a signal may further assist in the development of an immunological response. Other DC targeting studies have suggested that after antigen uptake, danger signals such as inflammatory cytokines (i.e., CD40 ligand) and/or activators of the Toll-like receptors (e.g., LPS and CpG DNA) are necessary to mature DCs and subsequently induce cell-mediated immunity [113-115]. Danger signals are identified as biomolecules that lead to upregulation of the gene NF-κB that in turn leads to maturation of APCs and release of inflammatory cytokines. In such a case a danger signal cytokines such as CD40 ligand, GM-CSF or a Toll-like receptor activator could be attached to a nanoparticle (e.g., at the core or surface layer or hydrophilic polymer layer), e.g., following previously described protocols for protein or peptide conjugation [109-111]. Moreover, a nanoparticle can be synthesized with an antigen and/or a non-complement danger signal attached to its surface.

Immunotherapy for Antibody Production

Some embodiments are directed to introducing an antigen to a patient to generate antibodies in the patient against the antigen. For example, vaccinations or antitumor therapies may be pursued in this manner. Alternatively, such approaches may be used to generate antibodies for use as scientific reagents, e.g., in animals.

Thus a combination of nanoparticle and antigen may be introduced into the patient. After a predetermined time (e.g., 1-30 days), a sample is taken from the patient and the antibodies against the antigen are measured. Additional samples and measurements may be periodically taken. If antibody titers are too low, the nanoparticles and antigens may be reintroduced and additional measurements made, with the process being repeated as necessary to bring antibody titers to a desired level. The combination may be administered several times.

Discussion of Experimental Results

Delivery of biodegradable nanoparticles to antigen-presenting cells (APCs), specifically dendritic cells (DCs) is documented herein, including applications for immunotherapy. Detailed examples herein describe the delivery of 20, 25, 45, and 100 nm diameter poly(ethylene glycol)-stabilized poly(propylene sulfide) (PPS) nanoparticles to DCs in the lymph nodes. The nanoparticles in the detailed examples comprise a cross-linked rubbery core of PPS surrounded by a hydrophilic corona of poly(ethylene glycol). The PPS domain is capable of carrying hydrophobic drugs and degrades to soluble polymer within oxidative environments. Peptide or protein antigens, including glycopeptide (defined herein as glycosylated polypeptides) antigens, and nucleic acid encoding antigens can be attached to the nanoparticle surface. 20 nm particles were most readily taken up into lymphatics following interstitial injection, while both 20 and 45 nm particles showed significant retention in lymph nodes, displaying a consistent and strong presence at 24, 72, 96 and 120 h post-injection. Nanoparticles were internalized by up to 40-50% of lymph node DCs (and APCs) without the use of an exogenous targeting ligand, and the site of internalization was in the lymph nodes rather than at the injection site. An increase in nanoparticle-containing DCs (and other APCs) was seen at 96 h vs. 24 h, showing an infiltration of these cells to lymph nodes. Both nanoparticle size and surface chemistry were found to influence DC maturation after in vivo injection.

The basic PPS nanoparticles as synthesized, i.e., PPS nanoparticle cores stabilized with PLURONIC (a block copolymer of polyethylene glycol (PEG) with polypropylene glycol), were found to activate DCs after in vivo injection of the nanoparticles, as indicated by increased expression of the maturation markers CD86, CD80 and CD40, when the nanoparticles were very small; 25 nm nanoparticles activated DCs extensively after in vivo injection, while 100 nm nanoparticles did not. When a second nanoparticle surface chemistry was utilized, i.e., PPS nanoparticle cores stabilized with a methoxy-terminated PLURONIC, even the very small nanoparticles did not activate DCs after in vivo injection. The PLURONIC-stabilized nanoparticles were demonstrated to effectively activate complement whereas the nanoparticles stabilized with methoxy-terminated PLURONIC were not effective to activate complement. Thus, nanoparticle complement activation induced DC activation after exposure to these nanoparticles.

Both nanoparticle size and surface chemistry were found to influence adaptive immunity after in vivo injection. Antigen was conjugated to PLURONIC-stabilized nanoparticle surfaces and was found to strongly induce antibody formation only when the nanoparticles were very small; 25 nm nanoparticles induced antibody formation much more strongly than 100 nm nanoparticles. When a second nanoparticle surface chemistry was utilized, i.e., PPS nanoparticle cores stabilized with a methoxy-terminated PLURONIC, even the very small nanoparticles did not induce strong antibody formation after in vivo injection. Moreover, when 25 nm PLURONIC-stabilized nanoparticles were injected in mice in which complement protein 3 had been knocked out (C3−/− mice), these nanoparticles did not strongly induce antibody formation. Thus, the detailed examples show that nanoparticles of suitable size, e.g., of 20-45 nm, have the potential for immunotherapeutic applications; for example, they may be used to specifically target and activate DCs in lymph nodes. Moreover, when these nanoparticles posses a surface chemistry that activates complement, such as obtained by stabilization by PLURONIC, they have strong potential for function as an antigen carrier and adaptive immunity-inducing adjuvant. The special combination of small size (e.g., 20-45 nm) and complement activation is valuable in vaccine formulations as an adjuvant.

The examples thus show that nanoparticles can be used for targeted antigen and drug delivery to APCs, specifically DCs, in lymph nodes. The simplicity of this approach is that by controlling size, nanoparticles can be effectively taken up into lymphatics as well as retained in lymph nodes (as shown, for at least 5 d), and without using any specific exogenous targeting ligand; they are internalized effectively by nodal resident DCs and other APCs (e.g., macrophages). Nanoparticles as large as about 45 nm or up to about 100 nm can not be effectively targeted into the lymphatics and the lymph node by this means. Additionally, it is demonstrated that up to about 40 to about 50% of resident lymph node DCs internalize nanoparticles, further demonstrating the effectiveness of this delivery vehicle. Also it was demonstrated that following exposure to nanoparticles of such size ranges as to be effectively targeted to the lymphatics, when those nanoparticles activate complement, the DCs respond by becoming more mature and inducing T cell dependant adaptive immunity. This is a clear demonstration of the potency of using the complement cascade as a danger signal in antigen presentation adjuvant formulations. It was demonstrated that the combination of small size (so as to effectively enter the lymphatics after administration) and complement activation (so as to stimulate APC including DC maturation) that strong adaptive immune responses could be induced, both T cell-dependant humoral (via Ab titers) and cellular (via the measurements of T-cell memory via T-cell proliferation and ELISPOT measurements). This special combination of small size and complement activation is very valuable in immunotherapeutics.

Example 1 describes emulsion polymerization techniques for making nanoparticles. These techniques may be applied to a variety of monomers/polymers to make suitable particles. Example 2 related to the modification of PLURONIC and is generally applicable to modifying other polymers herein, with variations being made to account for particular chemical structures.

EXAMPLES

Example 1

Nanoparticles

PPS nanoparticles with diameters of 20, 45, and 100 nm were synthesized by inverse emulsion polymerization as described elsewhere; in the term "emulsion polymerization" used herein, we include inverse emulsion polymerization, and in the term "emulsion", we include inverse emulsion [39]. Briefly, an emulsion was created by adding the PEG block copolymer emulsifier, PLURONIC F-127 (Sigma-Aldrich, Buchs, Switzerland) and the monomer propylene sulfide to ultrapure milliQ water under constant stirring. The protected initiator pentaerythritol tetrathioester was synthesized as described elsewhere [39] and, in a separate flask, was deprotected by mixing it with 0.20 mL of 0.5 M sodium methylate solution under stirring for 10 min. Following deprotection, the initiator was then added to the monomer emulsion and 5 min later 60 μl of the base diaza[5.4.0]bicycycloundec-7-ene (DBU) was added to the reaction and it was allowed to stir continuously for 24 h under an inert atmosphere. The nanoparticles were then exposed to air in order to produce disulfide cross-linking.

The nanoparticles were purified from remaining monomers, base, or free PLURONIC by 2 d of repeated dialysis with a 12-14 kDa MWCO membrane (Spectrum Laboratories, Rancho Dominguez, Calif.) against ultrapure milliQ water. The nanoparticle size distributions were determined by the use of a dynamic light scattering instrument (Malvern, Worcestershire, United Kingdom). Fluorescent labeling was accomplished by adding 6-iodoacetamido-fluorescein or Alexa Fluor 488 maleimide (Molecular Probes, Eugene, Oreg.) at 1 mg/ml of nanoparticle solution to the reactive thiols remaining on the nanoparticles, and then stirred in the dark for 6 h. The nanoparticles were then exposed to air for further disulfide cross-linking. Free iodoacetamido-fluorescein or Alexa Fluor maleimide was eliminated by repeated dialysis for 1 d using a 25 kDa MW cutoff membrane (Spectrum Laboratories) against 5 mM PBS.

Example 2

Synthesis of Methoxy-Terminated PLURONIC

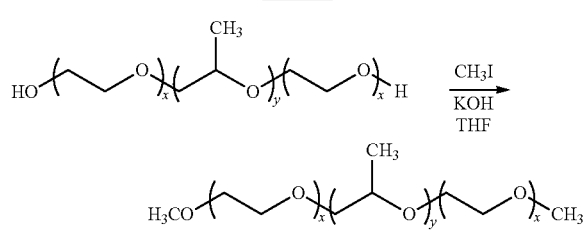

Scheme I

Pluronic F127 (Sigma), methyl iodide (Fluka), potassium hydroxide (Fluka), sodium thiosulfate penta hydrate (Riedel de Haen), anhydrous sodium sulfate (Applichem), sodium chloride (Sigma), diethylether (Fisher) and dichloromethane (Fisher) were used as received. Tetrahydrofuran stabilized with 0.025% BHT (Acros) was dried over molecular sieves before use. The reaction was carried out under argon (Messer) atmosphere. For dialysis a regenerated cellulose tube (Spectrapor) with molecular weight cut off 3400 was used. $^1$H NMR was measured in deuterated dimethylsulfoxide (Armar) and chemical shifts (δ) are given in ppm relative to residual solvent signal at 2.5 ppm.

To a solution of 10.0 g (0.79 mmol) PLURONIC F127 in 100 ml THF was added 2.99 g (53.3 mmol) finely ground potassium hydroxide and 988 μl (15.9 mmol) methyl iodide and the mixture stirred in the dark for 19 h. The clear solution is decanted and 3.94 g sodium thiosulfate penta hydrate, 100 ml saturated aqueous sodium chloride solution and 100 ml dichloromethane is added. The mixture was stirred vigorously and transferred to a separating funnel. The layers were separated and the aqueous phase extracted with dichloromethane (2×100 ml). The organic fractions were combined, dried over sodium sulfate and concentrated under reduced pressure. The solid was dissolved in a minimum amount of bidistilled water and dialyzed against 4500 ml water for one day. The clear aqueous solution is saturated with sodium chloride and extracted with dichloromethane (3×100 ml) and dried over sodium sulfate. After solvent removal the residue is extracted in a soxhlet extractor with diethylether for 6 h to yield after drying under reduced pressure 9.25 g of white solid. NMR showed the absence of the OH group at 4.6 ppm and the presence of the OCH$_3$ group at 3.2 ppm. δ=1.1 (d, CH$_3$, PPG), 3.2 (s, OCH$_3$) 3.3 (m, CH, PPG), 3.4 (m, CH$_2$, PPG), 3.5 (m, PEG).

Example 3

Animals

Unless otherwise stated, BALB/c mice, 6-9 weeks old and weighing 20-30 g, were used for this study. All protocols were approved by the Veterinary Authorities of the Canton Vaud according to Swiss law. Anesthesia was delivered by subcutaneous injection of ketamine hydrochloride at 10 mg/kg and xylazine at 1 mg/kg. Mice were euthanized by CO$_2$ asphyxiation.

Example 4

Microlymphangiography

To determine the relative uptake characteristics of the nanoparticles following interstitial injection into the skin, fluorescence microlymphangiography was performed by constant pressure injection into the tip of the tail as previously described [43-45]. Hair was depilated from the mouse tail, and the mouse was positioned on the microscope stage (Axiovert 200M, Zeiss) with a heating pad to maintain 37° C. body temperature. A 20 mg/ml solution of fluorescent PPS nanoparticles (20, 45, or 100 nm diameter) in sterile phosphate-buffered saline (PBS) was drawn into a catheter; a 30-gauge needle attached to the catheter was inserted intradermally at ~1 mm from the tail tip and a stopcock was opened that initiated flow at a constant pressure of 40 mm Hg. The flow rate of the nanoparticle solution (monitored with a bubble far upstream in the tubing) averaged 0.1 μl/min into roughly 20 mm$^3$ of tissue (approximated from the volume visible from the injection depot), or approximately 5 μl/g/min. No visible swelling was observed. Sequential images along the length of the tail were collected at a constant exposure time; 3 experiments were repeated for each nanoparticle size.

Fluorescence microlymphangiography in the mouse tail was used to evaluate the lymphatic uptake of PPS nanoparticles of 20, 45, and 100 nm diameter. Following infusion with 20 nm particles, the hexagonal lymphatic capillary network was clearly visible after 90 min and uniformly filled from the injection site (FIG. 1a). In contrast, only a very faint lymphatic network was observed following injection with the 45 nm particles (FIG. 1b), and very little network could be seen with the 100 nm particles (FIG. 1c), indicating poor uptake. The upper limit of size for macromolecule/protein/particle leakage into blood capillaries is well known to be ~3.5 nm [42], therefore the leakage into blood vasculature of our smallest 20 nm particles is effectively zero. This method thus qualitatively confirms that 20 nm particles are more readily taken up into the lymphatic capillaries from the interstitial space compared to 45 nm and 100 nm particles.

Example 5

Evaluation of Nanoparticle Distribution in Lymph Nodes: Lymph Node Retention of Small Nanoparticles (e.g., 20-45 nm)

To evaluate lymph node retention, 20 μl of 20 mg/ml fluorescent PPS nanoparticles (20, 45, and 100 nm diameter)

were injected as a bolus into the tip of the mouse tail or front footpad through a 30 gauge needle; controls were performed with 20 µl injections of PBS. No inflammation was observed at the sites of injection. At 24, 72, 96, or 120 h, mice were sacrificed by $CO_2$ asphyxiation. The sacral and lumbar lymph nodes, which drain the tail and leg lymphatics, brachial and axillary lymph nodes, which drain the front footpad area lymphatics were removed, flash frozen, cryosectioned into 10 µm sections, and immunostained with antibodies against mouse CD3e (Pharmingen, San Diego, Calif.), CD45R (Caltag, Burlingame, Calif.), CD68 (Serotec, Dusseldorf, Germany), Dec-205 (Serotec), and CD31 (Pharmingen) to label T cells, B cells, macrophages/DCs, DCs, and endothelial cells, respectively. Secondary detection was performed with Alexa Flour 594 nm (Molecular Probes) antibodies. Lymph node sections were imaged with fluorescence (Axiovert 200M, Zeiss) and confocal laser scanning microscopy (LSM 510 Meta, Zeiss).

Figure 2:
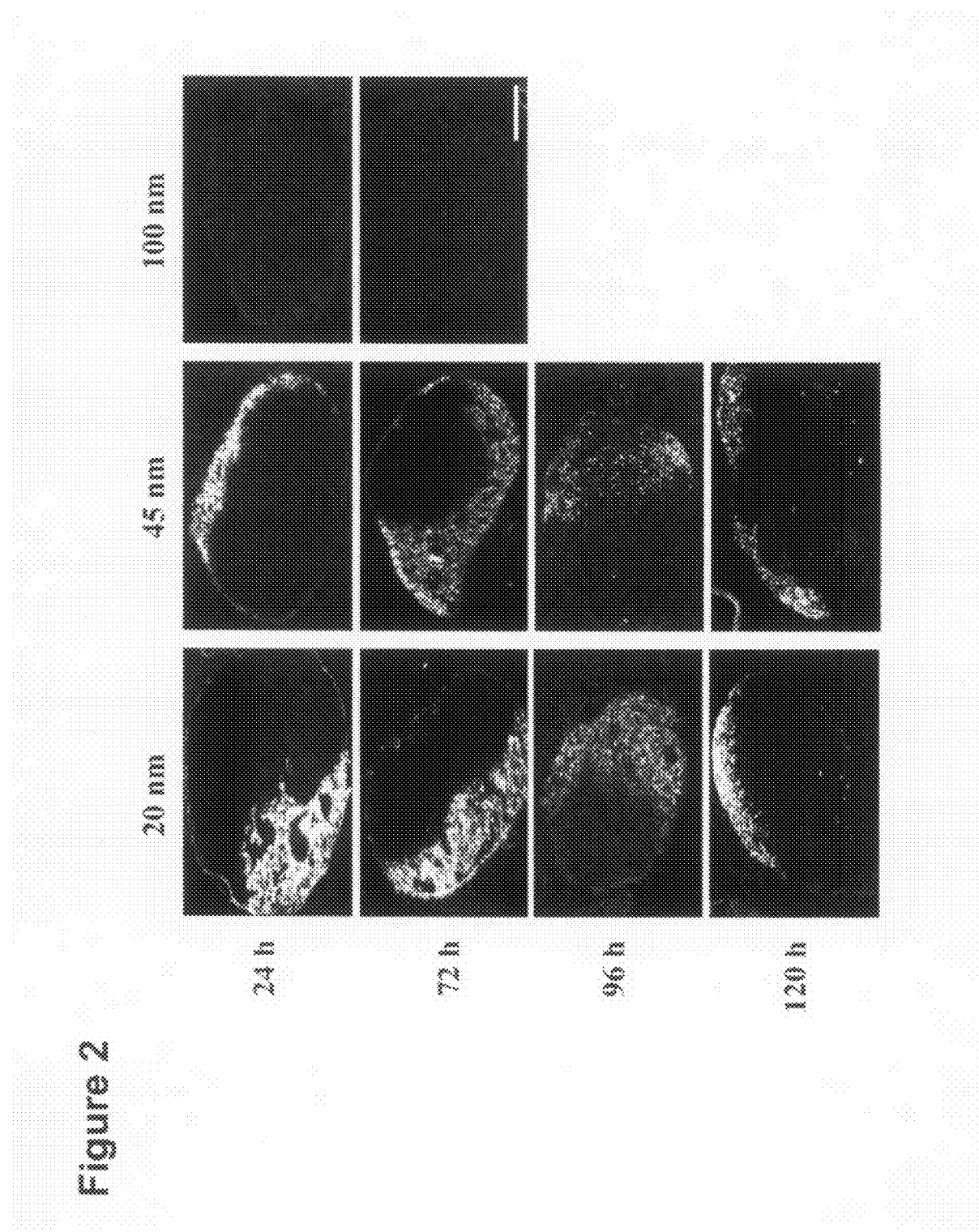
FIG. 2 is a photomicrographic montage showing lymph node retention of nanoparticles. Shown are sections from draining lymph nodes following injections into the mouse tail with 20, 45, and 100 nm PPS nanoparticles. Lymph nodes were removed at 24, 72, 96, and 120 h post-injection. Nanoparticles were strongly present at all time points for 20 and 45 nm nanoparticles, but 100 nm particles were not seen in the lymph nodes. Bar=200 μm.

Lymph node retention time of nanoparticles and liposomes has been investigated by several other researchers for purposes of studying the lymphatic system and typically has focused on time points in the range of 6-52 h post-injection [31-34, 36]. Examples reported herein described lymph node retention of nanoparticles up to 120 h, and showed that 20 nm particles were significantly present at qualitatively consistent levels in the lymph node at 24, 72, 96, 120 h following a bolus injection of 20 µl intradermally (FIG. 2). The 45 nm nanoparticles were also present, although in lower amounts, in lymph nodes at all time points, while the 100 nm nanoparticles were not visibly present in the lymph nodes at any time point (FIG. 2). Thus, together with the results in FIG. 1, these data show that 20-45 nm is a good PPS nanoparticle size range for both lymphatic uptake and lymph node retention, with 20 nm being optimal, while 100 nm particles are too large for efficient lymphatic uptake from the interstitium following a constant pressure injection. This is consistent with previous studies that have shown liposomes >70 nm remain mostly at the site of injection [24, 30].

Figure 3:
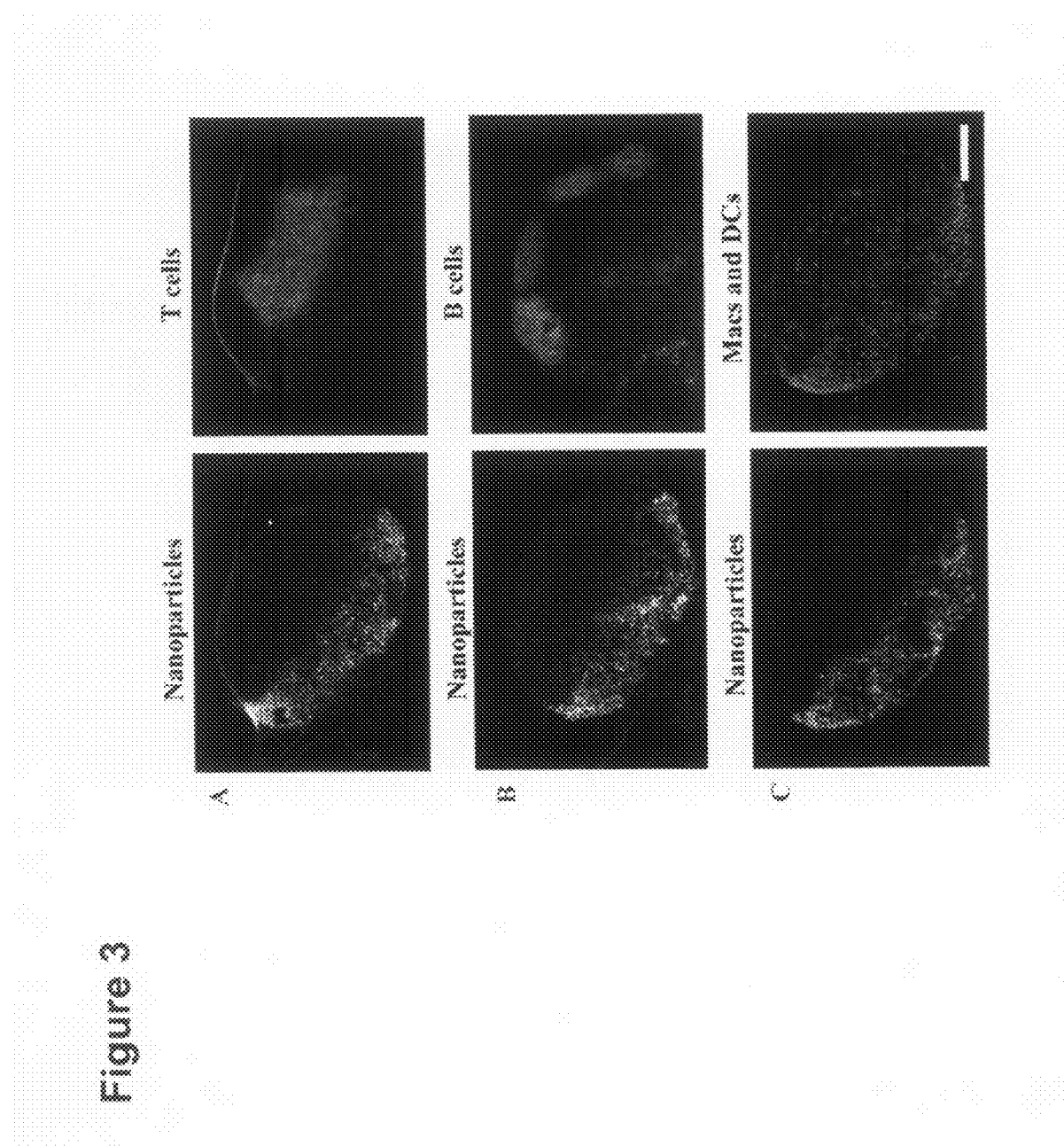
FIG. 3 is a photomicrographic montage showing localization of nanoparticles within the lymph node. Shown are serial lymph node sections at 96 h following injection of 20 nm PPS nanoparticles. Immune cells were identified as indicated with antibodies against (A) CD3e (T cells), (B) CD45R (B cells), and (C) CD68 (macrophages (Macs) and dendritic cells (DCs)). Nanoparticles are distinctly absent in T cell and B cell zones, but strongly co-localized with macrophages and DCs. Bar=100 μm. (D) The endothelial marker CD31 demonstrates nanoparticle (green) distribution relative to lymph node sinus architecture. Bar=100 μm.

The specific locations, with respect to the various immune cells, in which PPS nanoparticles accumulated within lymph nodes, were evaluated. Staining results were consistent with known lymph node architecture, where specific zones for T and B lymphocytes can be readily seen [2]. T cells tend to aggregate in the center regions of the node while B cells are often found in germinal centers located towards the outer membrane. The other major cell types present in lymph nodes are APCs or MHCII$^+$ cells, namely DCs and some macrophages, and their location is often more dispersed. FIG. 3 shows serial sections of the same lymph node following an intradermal injection of 20 nm particles. The nanoparticles were not present in the T cell or B cell zones (FIG. 3a, b). However, there was significant co-localization of the nanoparticles with macrophages and DCs; i.e., CD68$^+$ cells (FIG. 3c).

Figure 4:
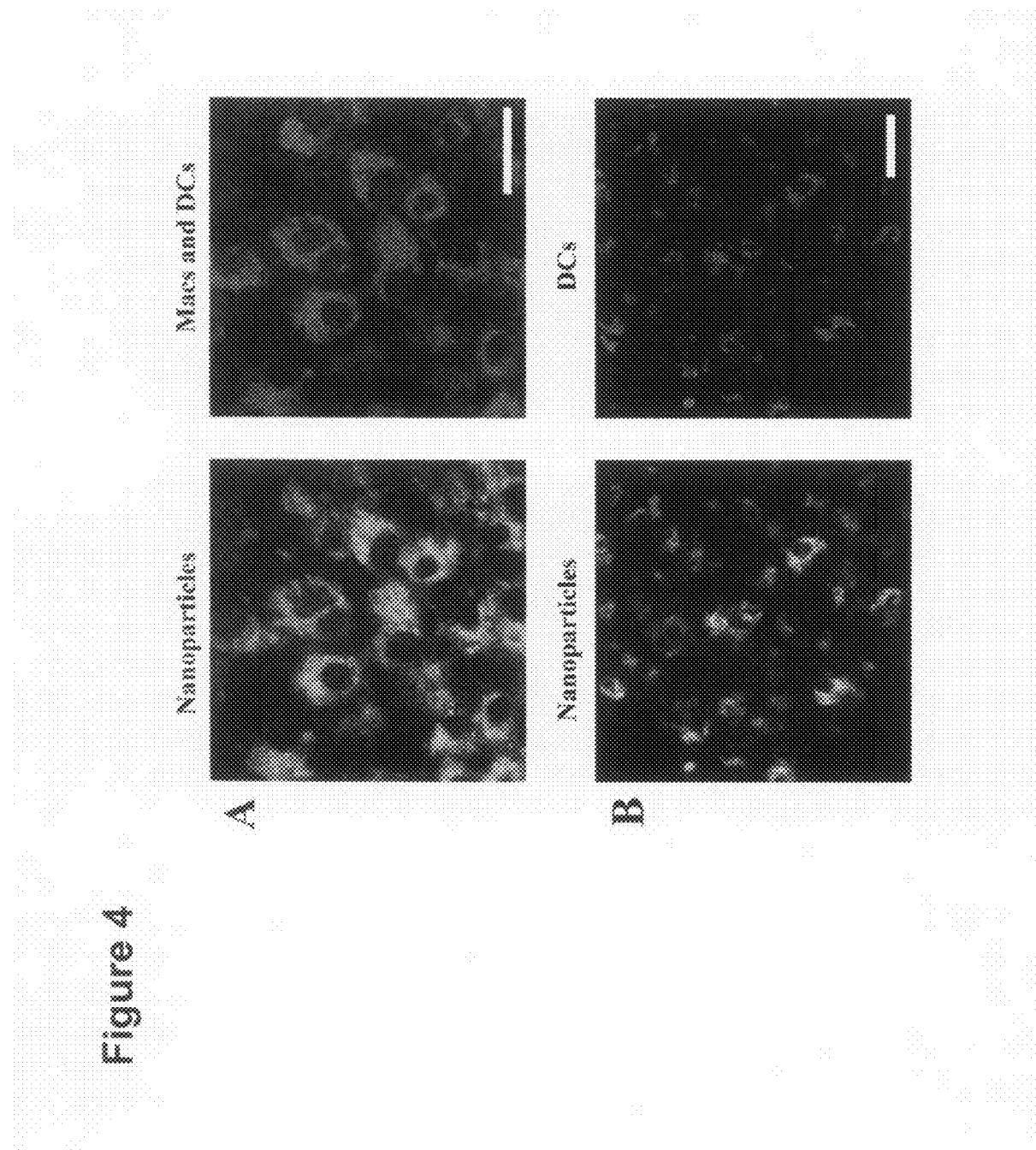
FIG. 4 is a photomicrographic montage showing internalization of nanoparticles by macrophages and dendritic cells (DCs). Shown are confocal images of lymph node sections at 96 h following injection of 20 nm PPS nanoparticles. (A) Staining for CD68, expressed by both macrophages and DCs, reveals internalization of nanoparticles by these cells. (B) Staining for Dec-205, which is found exclusively on DCs, demonstrates that DCs also internalize the nanoparticles. Bar=20 μm.

It has generally been assumed that liposomes and nanoparticles delivered to lymph nodes are primarily phagocytosed by macrophages there [21, 27, 29, 30, 32, 36, 37]. However, it has not been appreciated in these arts that immature DCs capable of taking up antigens are also present in the lymph nodes [15, 16]. With PPS nanoparticle delivery, immunostaining for CD68 (which, although a transmembrane protein, is also expressed intracellulary [47-50]) verified that macrophages and DCs had internalized PPS nanoparticles (FIG. 4a). To further determine whether the CD68$^+$ cells were macrophages, DCs, or both, lymph nodes were immunostained for the highly-specific DC receptor Dec-205 [4, 38, 51-56]. The Dec-205$^+$ cells and their co-localization with nanoparticles (FIG. 4b) demonstrate that a significant fraction of the cells in the lymph node that phagocytose the nanoparticles were, indeed, DCs. This will be advantageous for delivering antigens to lymph nodes in order to stimulate APCs, including the most potent APC type—DCs.

Example 6

Lymph Node Cell Isolation and Staining

Lymph node cells were isolated following a previously described protocol [46]. Briefly, following injections of fluorescent nanoparticles or PBS as described earlier, lymph nodes were removed, teased with 26 gauge needles and digested in Collagenase D (Roche, Basel, Switzerland) for 25 minutes at 37° C. Tissue was then passed through a 70-µm cell strainer (BD, Basel, Switzerland) to recover a cell suspension. With the lymph node cell suspension, APCs were stained for with anti-MHC Class II-(I-A)-R-PE (Chemicon, Temecula, Calif.) and DCs with anti-CD11c-allophycocyanin (Pharmingen). DC maturation was measured by staining with anti-CD 86-R-PE and anti-CD80-R-PE (Pharmingen).

Example 7

In Vitro Nanoparticle Internalization

Following lymph node cell isolation, cells were plated in RPMI (5% FBS) at ~500,000 cells/ml. Cells were then pulsed with 20 µl of 20 mg/ml of fluorescent nanoparticles and incubated for 24 h. Cells were then washed twice with HBSS and stained for APCs and DCs as mentioned earlier.

Example 8

Flow Cytometry & Analysis and In Vitro Nanoparticle Internalization: Uptake by APCs, Including DCs Following staining, lymph node cell suspensions were analyzed by flow cytometry (CyAn ADP, Dako, Glostrup, Denmark). Further analysis was performed using FlowJo software (TreeStar, Ashland, Oreg.). APCs and DCs that had internalized fluorescent nanoparticles were determined to be MHCII$^+$FITC$^+$ and CD11c$^+$FITC$^+$, respectively, FITC representing labeling of the nanoparticles. DC maturation following nanoparticle internalization was evaluated by calculating the fraction of cells that expressed CD86 and CD80.

Figure 5:
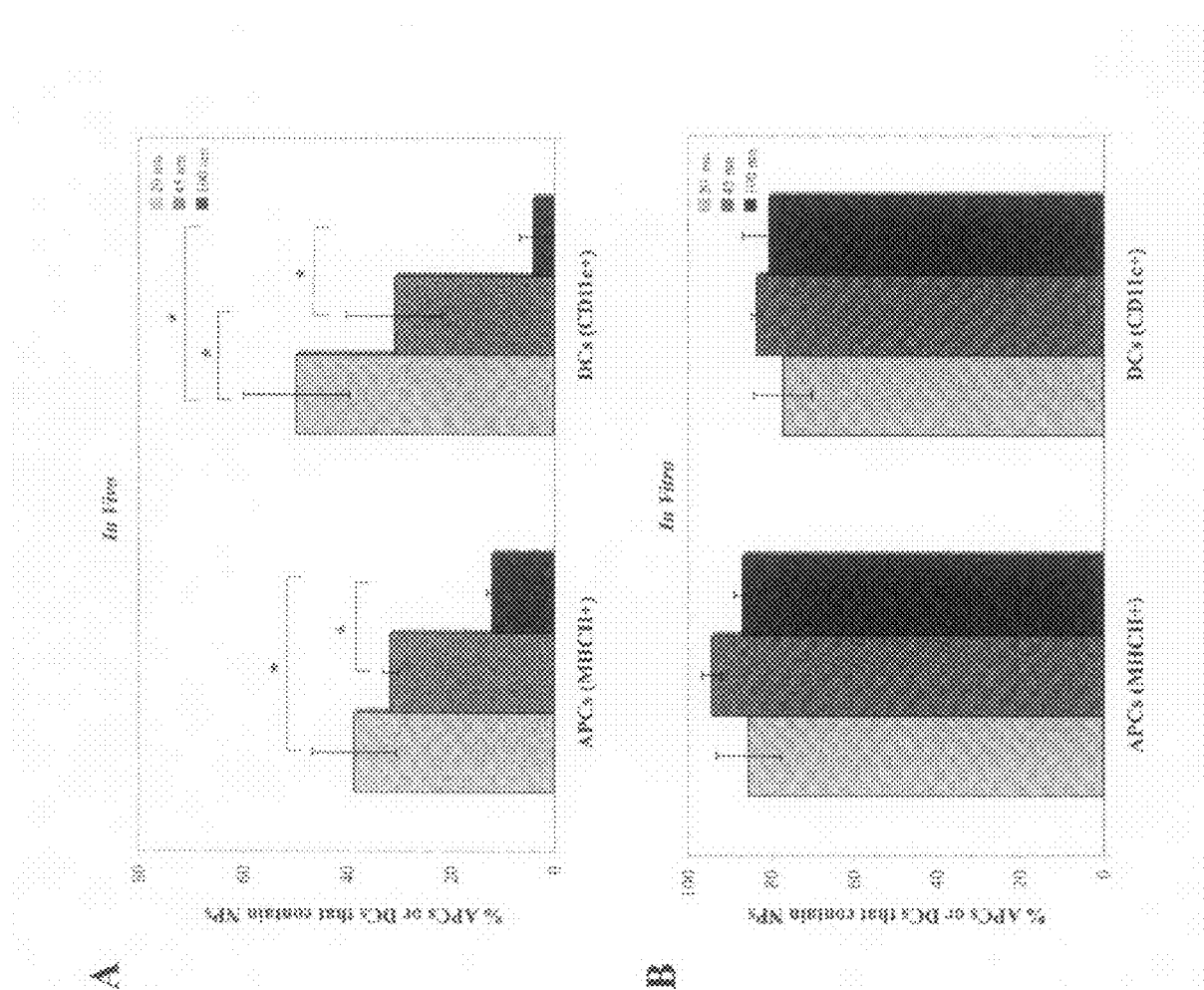
FIG. 5 has bar graphs that show quantification of cell uptake of nanoparticles (NPs). Flow cytometry analysis was used to determine the fraction of lymph node APCs (MHCII+) and DCs (CD11c+) that internalized NPs (FITC+). (A) At 24 h, following injections, more than 38% of APCs and 50% of DCs in lymph nodes had internalized 20 nm nanoparticles. There was reduced uptake in both cell populations with 45 nm nanoparticles, and only ~10% of all APCs took up 100 nm nanoparticles. (B) After in vitro pulsing of APCs and DCs with nanoparticles for 24 h, nearly all APCs and DCs had internalized nanoparticles of all 3 sizes. Thus since all 3 nanoparticle sizes are equally taken up in vitro, the differences seen following in vivo injection are most likely due to differences in nanoparticle uptake into lymphatics following injection. These results also indicate that nanoparticle uptake occurs in the lymph nodes rather than by cells in peripheral sites, which then migrate to lymph nodes.

Flow cytometry analysis was performed to quantify the fraction of APCs and DCs in lymph nodes that were internalizing nanoparticles. FIG. 5a shows that up to ~40% of APCs (MHCII$^+$) and specifically ~50% of DCs (CD11c$^+$) in lymph nodes have taken up 20 nm nanoparticles after 24 h postinjection. Accordingly, and in general, nanoparticle applications with at least at 10% to about 95% uptake by APCs and/or DCs are contemplated; artisans will immediately appreciate that all the ranges and values within the explicitly stated ranges are contemplated, e.g., at least about 25%, at least about 40%, or between about 25% and about 75%/50%. Also a significant fraction of APCs and DCs phagocytose 45 nm nanoparticles while very little uptake of 100 nm nanoparticles was observed after in vivo injection. APCs, including the DCs, could have either endocytosed the particles after they arrived in the lymph node, or internalized them at the injection site before trafficking to lymph nodes. If the latter were the case, 100 nm particles would be seen in the lymph node, since larger particles (1-10 µm) can be endocytosed by APCs just as efficiently as smaller ones [13, 57]. It was verified that nanoparticle size did not affect APC or DC internalization by in vitro experiments; nearly all APCs and DCs internalized nanoparticles regardless of size (FIG. 5b). Therefore PPS nanoparticles are likely taken up passively into peripheral lymphatic vessels and reach the lymph nodes, where they are phagocytosed by resident DCs or APCs. These results reinforce the recent findings that substantial numbers of immature DCs capable of internalizing antigens are present in lymph nodes [15, 16]. Indeed, DCs and other APCs in lymph nodes offer a valuable target for initiating cell-mediated immunity via drug delivery vehicles.

Figure 6:
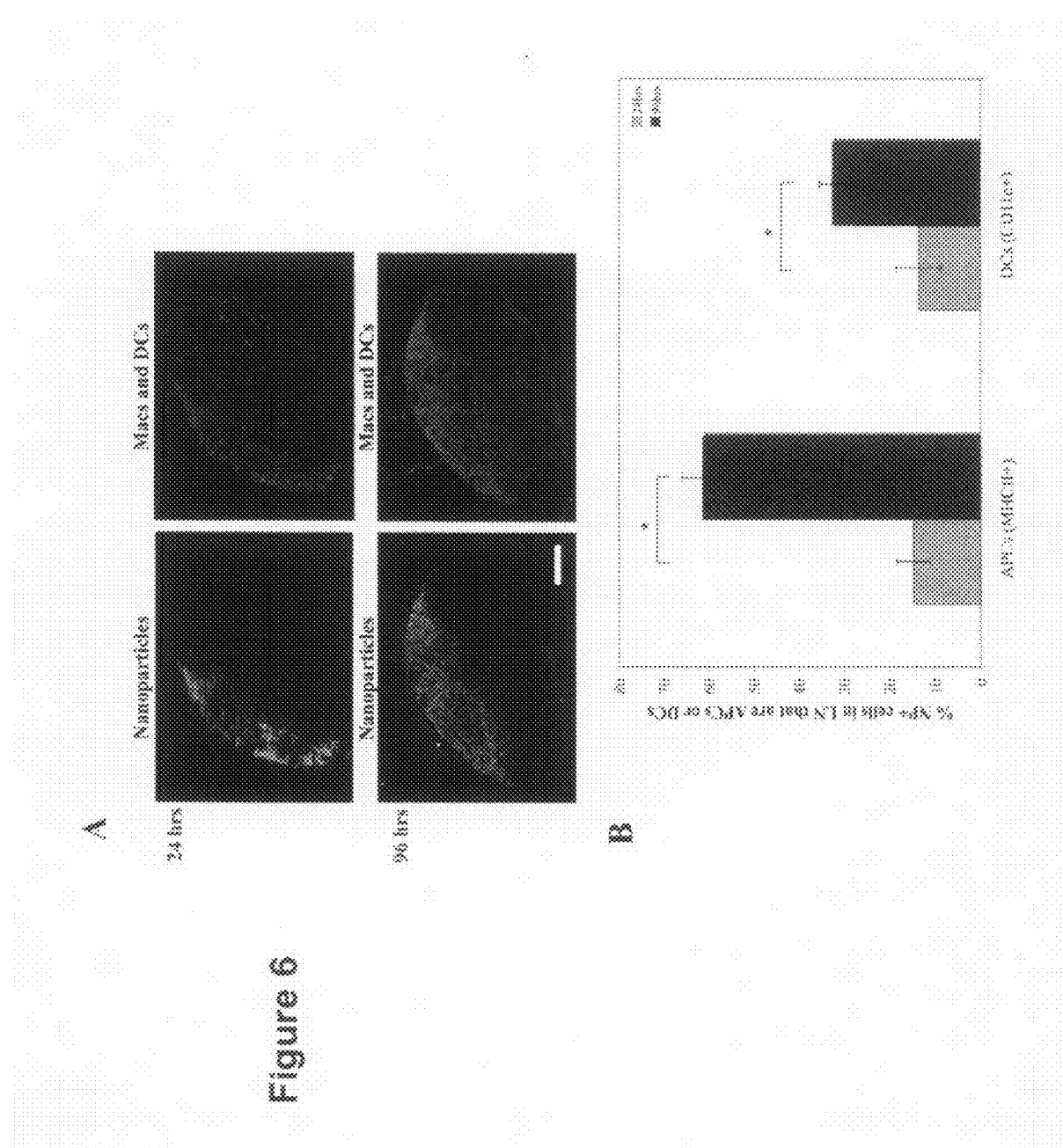
FIG. 6 is a (A) a photomicrographic montage and (B) bar graph that both show increase of presence of macrophages and dendritic cells (DCs) with time. Shown are lymph node sections stained for macrophages (Macs) and DCs (CD68+ cells) and nuclei at 24 and 96 h post-injection of 20 min PPS nanoparticles (NPs). Mac and DC co-localization increased with time. Bar=100 μm. (B) Flow cytometry analysis was used to determine the fraction of lymph node (LN) cells with nanoparticles (NPs+) that were APCs (MHCII+) and DCs (CD11c+) at 24 and 96 h post-injection of 20 nm nanoparticles. There is a significant increase in the fraction of cells with nanoparticles that are APCs and DCs at 96 h vs. 24 h. Also, it appears that nearly all APCs with nanoparticles at 24 h are DCs.

A comparison of nanoparticle internalization at different times was investigated. It was found that nanoparticle co-localization with macrophages and DCs was visibly higher at 96 h than at 24 h (FIG. 6a). Flow cytometry analysis was used to determine if there was a change in the type of macrophages and DCs internalizing nanoparticles at 96 h vs. 24 h. Of all cells that had internalized nanoparticles at 24 h, ~15% were APCs (MHCII$^+$) and ~13% were DCs (CD11c$^+$), suggesting that most of the APCs were DCs, and that the remaining ~85% of nanoparticle containing cells were non-antigen presenting macrophages (vamp. At 96 h, the fraction of cells with nanoparticles that were APCs or DCs was 61±5% and 33±3%, respectively (Note that this does not reflect an increase in the fraction of lymph node APCs and DCs that contain nanoparticles, which remains constant at levels shown in FIG. 5a). The increase in nanoparticle-containing MHCII$^+$ and CD11c$^+$ cells may be due to an infiltration of APCs and DCs into lymph nodes that then pick up free nanoparticles still remaining in the nodal tissue. It is also possible that the increase in MHCII+ cells with nanoparticles is due to the activation of macrophages between 24-96 h (i.e., MHCII$^-$ macrophages that become activated and thus MHCII$^+$ following nanoparticle internalization).

Figure 7:
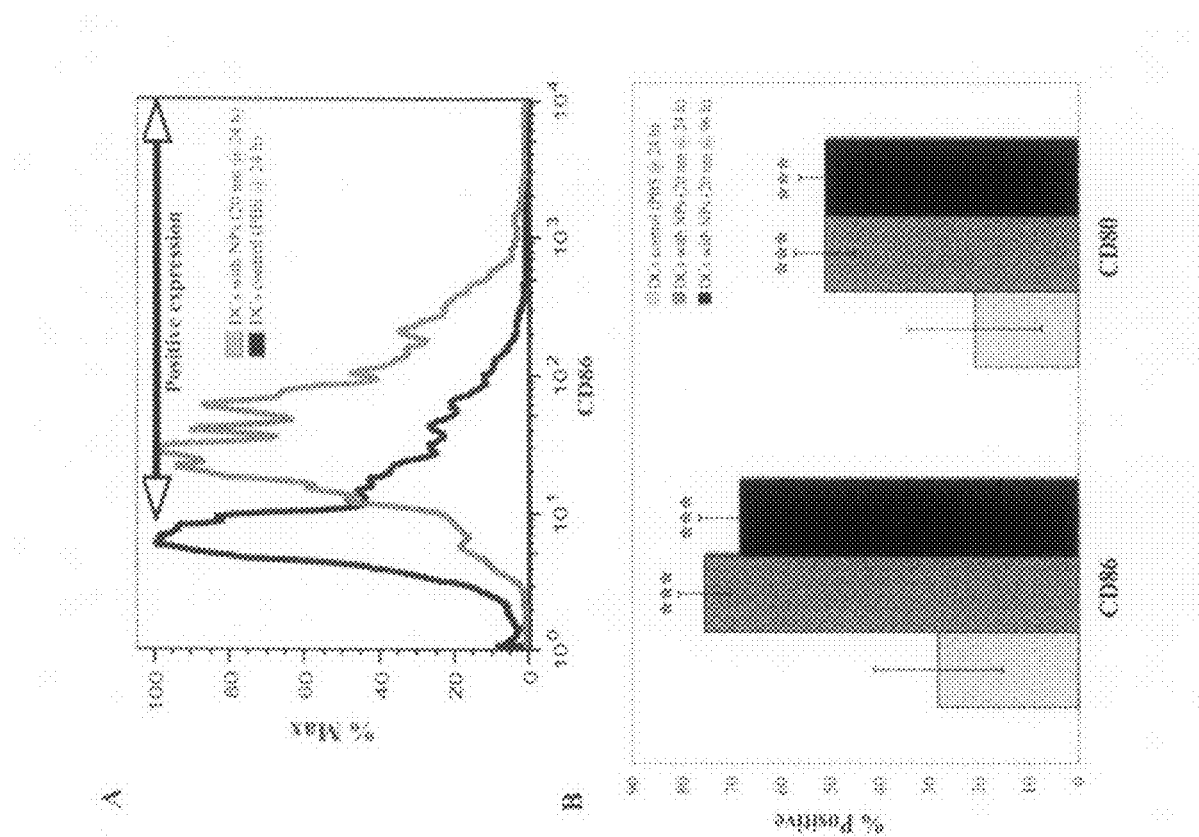
FIG. 7 depicts graphs that show an increase in expression of DC maturation markers, CD86 and CD80 following nanoparticle (NP) internalization. (A) A typical histogram of CD86 expression of DCs (CD11c+) at 24 h post-injection with PBS or 20 nm particles. A clear shift in CD86 expression is observed for DCs with nanoparticles (CD11c$^+$FITC$^+$). (B) The fraction of cells positively expressing CD86 and CD80 is determined to be significantly greater following nanoparticle internalization. Additionally it is shown that CD86 and CD80 expression remains at higher levels at 96 h post-injection.

A significant fraction of DCs in lymph nodes are already mature, however since there are immature DCs present, it is likely that these cells become mature following antigen uptake. Therefore it was determined if 20 nm PLURONIC-stabilized complement-activating (and thus hydroxylated) PPS nanoparticles help induce DC maturation such that conventional biological exogenous "danger signals" were not necessary when used in combination with the PLURONIC-stabilized complement-activating PPS nanoparticles. Following injections of 20 nm PLURONIC-stabilized complement-activating nanoparticles, the expression of the DC maturation marker CD86 was increased compared to controls that received injections of PBS (FIG. 7). The DC expression of CD80 was also measured and determined to be significantly greater following nanoparticle internalization (FIG. 7b). Finally it was found that the expression levels of CD86 and CD80 in DCs with nanoparticles did not change at 96 h vs 24 h post-injection. This suggests that the 20 nm PLURONIC-stabilized complement-activating nanoparticles offer a prolonged maturation stimulus, which could be useful for maintaining T cell activation and cell-mediated immunity over a prolonged time period. Therefore these results show that PLURONIC-stabilized complement-activating PPS nanoparticles may serve a dual role, acting as a vehicle for DC specific antigen delivery and also as an adjuvant that matures and activates DCs in lymph nodes.

Example 9

C3a Detection in Human Serum 96 well plates (Becton Dickinson) were coated with C3a/C3a (desArg) mouse anti-human monoclonal antibody (AntibodyShop, Grusbakken, Denmark) at 1:4000 dilution in PBS at 100 µl/well. Plates were left overnight at room temperature (RT). Unbound antibody was flicked off (i.e., removed by sudden mechanical motion) and the plate was washed 3× with 200 µl/well DI water. Plates were then blocked for 1.5 h at RT with 200 µl/well blocking buffer (PBS+Tween20 at 0.05%+Bovine serum albumin at 0.5%).

Human serum was incubated at 1:1 volume with PBS, suspensions of nanoparticles stabilized with PLURONIC (and thus hydroxylated nanoparticles), and suspensions of nanoparticles stabilized with methoxy-terminated nanoparticles (and thus not hydroxylated nanoparticles) in Eppendorf tubes at 37° C. for 45 min. When plates were finished blocking, they were washed 3× with 250 µl/well wash buffer (PBS+Tween20 at 0.05%). Serum-nanoparticle samples were then added to wells in triplicate at a 50 µl/well for 2 h at RT. Samples were then flicked out and plate is then washed with wash buffer 5× at 250 µl/well. C3a/C3a (desArg)-biotinylated detection antibody (AntibodyShop) was then added at 1:4000 dilution in blocking buffer at 50 µl/well for 2 h at RT. C3a detection antibody was then flicked out and the plate was washed with wash buffer 5× at 250 µl/well. Next streptavidin-HRP antibody (R&D systems) was diluted in blocking buffer at concentration recommended by manufacturer and added to plate at 50 µl/well for 2 h at RT. HRP antibody was then flicked out and the plate was washed with wash buffer 5× at 250 µl/well. Next, HRP substrate reagent (R&D systems) was added at 100 µl/well in the dark for 45 min at RT. The reaction was stopped by adding 50 µl/well of 2N H$_2$SO$_4$. The plate was then read on Tecan plate reader at 450 nm and 540 nm wavelength. The 540 nm background values were subtracted from 450 nm to obtain final values.

Figure 8:
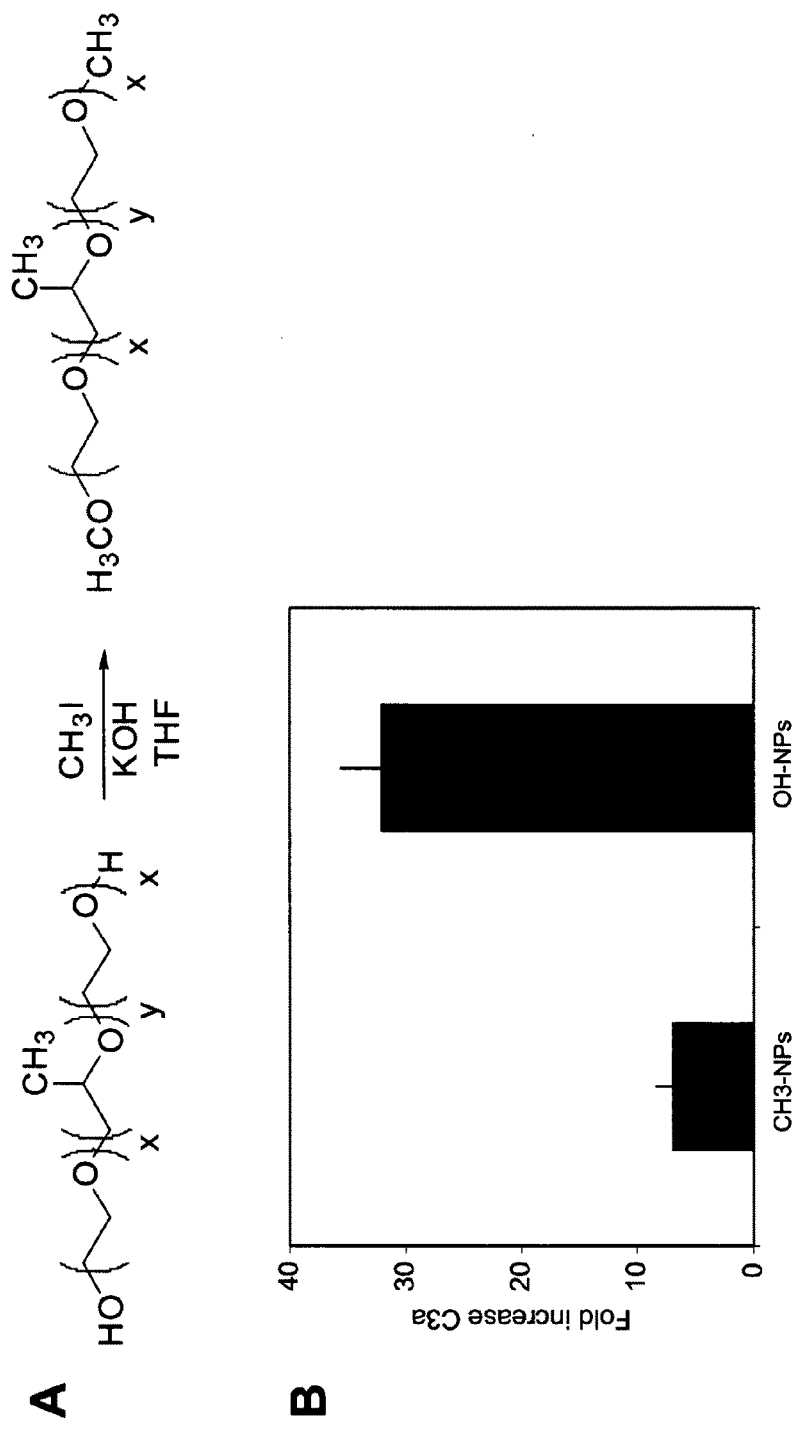
FIG. 8 depicts data showing that PLURONIC F-127 is modified so that the terminal OH groups are converted to $OCH_3$ groups (A). (B) Incubation of PLURONIC-stabilized (and thus hydroxylated) complement-activating nanoparticles (OH—NPs) with serum causes greater complement activation than nanoparticles stabilized with methoxy-terminated PLURONIC ($CH_3$—NPs) measured through fold increase of C3a in serum+PBS.

The C3a present in serum incubated with PBS was compared to C3a present following incubation with PPS nanoparticles stabilized with PLURONIC (and thus hydroxylated nanoparticles) and PPS nanoparticles stabilized with methoxy-terminated PLURONIC (and thus not hydroxylated nanoparticles). Incubation with the PPS nanoparticles stabilized with methoxy-terminated PLURONIC lead to ~7 fold increase, and incubation with the PPS nanoparticles stabilized with PLURONIC lead to a ~32 fold increase of C3a present in serum with PBS, as shown in FIG. 8. The hydroxylated nanoparticles thus activated the complement system much more than non-hydroxylated nanoparticles as measured by the cleavage of human serum C3 into soluble C3a and bound C3b. This confirms that the nanoparticle's OH surface is activating the alternative pathway of the complement system far more efficiently than a methoxy surface.

Example 10

Surface Chemistry Effects on DC Maturation 25 nm PLURONIC-stabilized nanoparticles (and thus hydroxylated nanoparticles; produced as described herein), 25 nm nanoparticles stabilized with methoxy-terminated PLURONIC (and thus not hydroxylated) nanoparticles, 20 nm carboxylated polystyrene nanospheres (COOH—NSs) (Invitrogen), PBS, and LPS (30 µg) were injected intradermally into mice as previously described. Lymph nodes were then harvested and cells are isolated and stained for CD11c, CD86, CD80, and CD40 as previously described. Flow cytometry was performed to determine maturation profile of lymph node DCs.

Figure 9:
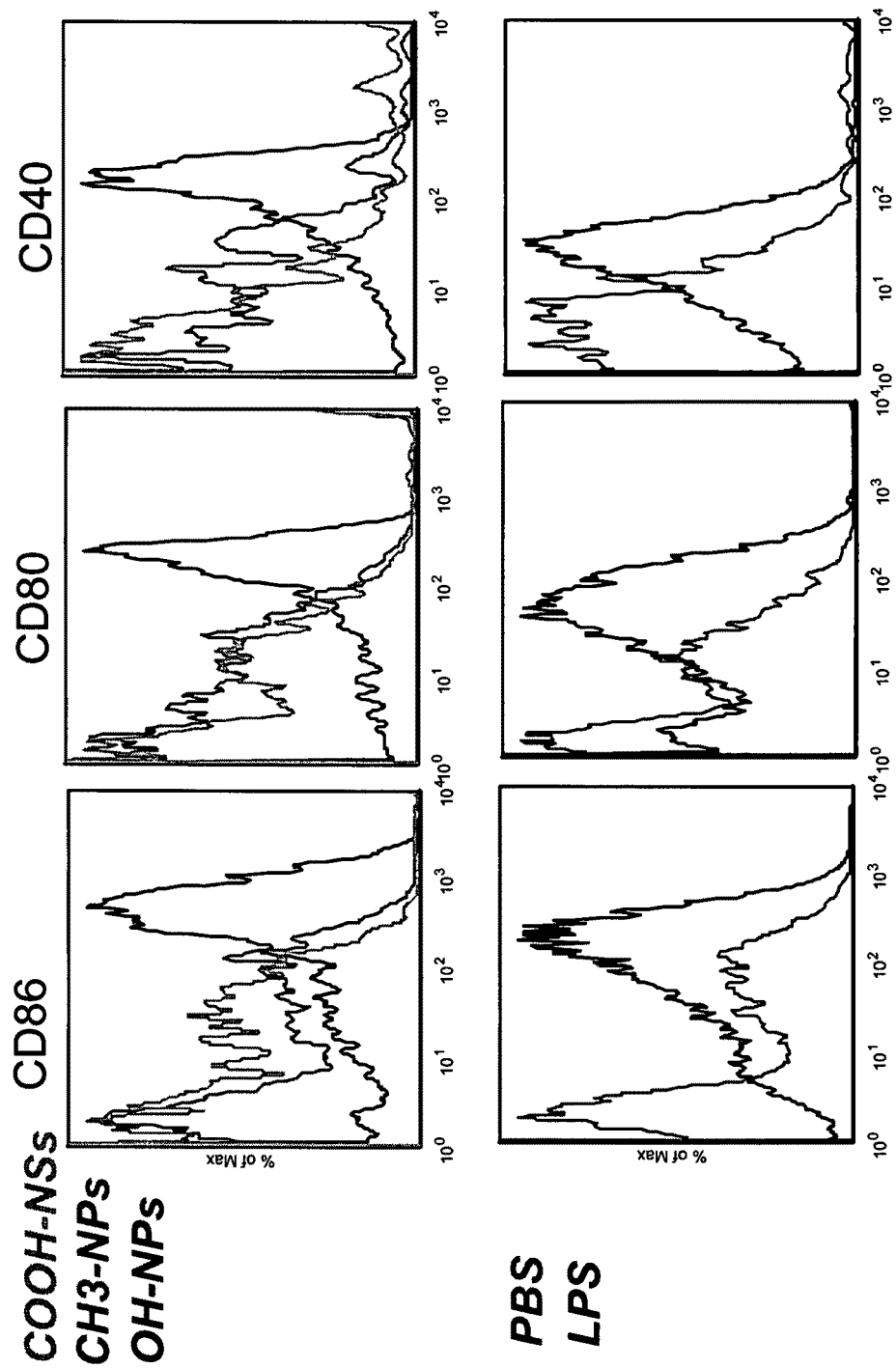
FIG. 9 depicts graphs showing that nanoparticle surface chemistry dictates DC maturation response. 25 nm PLURONIC-stabilized (and thus hydroxylated) complement activating nanoparticles (OH—NPs) mature DCs to a much greater extent than 25 nm nanoparticles stabilized with methoxy-terminated PLURONIC ($CH_3$—NPs) and 20 nm carboxylated polystyrene nanospheres (COOH—NSs).

As seen in FIG. 9, the CD86, CD80, and CD40 profiles for PLURONIC-stabilized (and thus hydroxylated) nanoparticles compared to methoxy-terminated PLURONIC-stabilized nanoparticles (and thus not hydroxylated) nanoparticles and to carboxylated polystyrene nanospheres are significantly different. The DCs from animals treated with PLURONIC-stabilized nanoparticles show higher expression of these DC maturation markers, furthermore they induce maturation to similar levels as the positive control LPS. The DCs from animals treated with methoxy-terminated PLURONIC-stabilized nanoparticles and from animals treated with carboxylated polystyrene nanospheres yielded nearly identical DC maturation responses as negative control PBS injection. These results show that the DC maturation response in vivo is specifically dictated by the surface chemistry of 20-25 nm nanoparticles. The hydroxylated surface induces DC maturation while the methoxy and carboxyl surfaces do not. Based on the results presented herein, the functional difference in these surfaces is in complement activation by the hydroxylated surfaces.

Example 11

Size Effects on DC Maturation 25 nm PLURONIC-stabilized (and thus hydroxylated) nanoparticles, and 100 nm PLURONIC-stabilized (and thus hydroxylated) nanoparticles, and PBS were injected intradermally into mice as previously described. Lymph nodes were then harvested and cells were isolated and stained for CD11c, CD86, CD80, and CD40 as described herein. Flow cytometry was performed to determine maturation profile of lymph node DCs.

Figure 10:
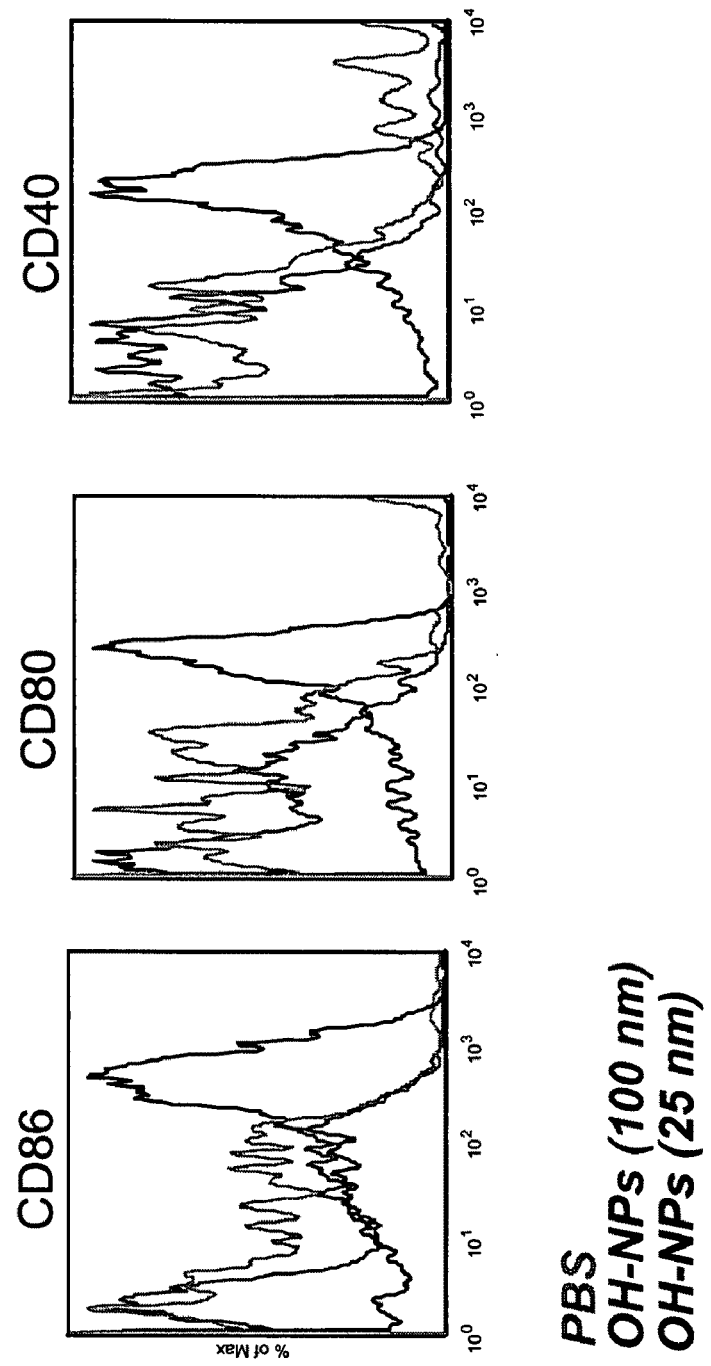
FIG. 10 depicts graphs showing that nanoparticle size dictates DC maturation response. 25 nm PLURONIC-stabilized (and thus hydroxylated) complement activating nanoparticles (OH—NPs) induce DC maturation, whereas 100 nm PLURONIC-stabilized (and thus hydroxylated) complement activating nanoparticles do not.

As seen in FIG. 10, the CD86, CD80, and CD40 profiles for 25 nm PLURONIC-stabilized (and thus hydroxylated) nanoparticles compared to 100 nm of the same surface chemistry are significantly different. The 25 nm PLURONIC-stabilized nanoparticles show higher expression of these DC maturation markers. The 100 nm PLURONIC-stabilized nanoparticle injections yielded nearly identical DC maturation responses as negative control PBS injection. These results show that the DC maturation response in vivo is specifically related to nanoparticle size. It has been described herein that 25 nm PLURONIC-stabilized nanoparticles efficiently enter lymphatic capillaries and traffic to lymph nodes to much greater extent than 100 nm PLURONIC-stabilized nanoparticles. Also the retention of 25 nm PLURONIC-stabilized nanoparticles and internalization by DCs in lymph nodes is much greater than that of 100 nm PLURONIC-stabilized nanoparticles. Here it is shown that also the DC maturation is much greater with 25 nm PLURONIC-stabilized nanoparticles compared to 100 nm PLURONIC-stabilized nanoparticles. The ability of ultrasmall 25 nm PLURONIC-stabilized nanoparticles to induce DC maturation demonstrates that lymph node targeting and surface chemistry are useful to activate DCs. Based upon the results on entry of nanoparticles into the lymphatic capillaries presented herein, it is expected that 45 nm PLURONIC-stabilized (and thus hydroxylated) nanoparticles can activate DCs within the lymph node.

Example 12

OVA Conjugation to Nanoparticles

Antigen conjugation to PPS nanoparticles can be accomplished by functionalizing Pluronic (a block co-polymer of PEG and PPG) surface with proteins or peptides, including glycopeptides. A conjugation scheme is presented in this example for a protein antigen that contains a free cysteine residue for chemical conjugation. Other functionalities can be used in related schemes, such as amines at the N-terminus or on lysine residues. Antigen may also be adsorbed to nanoparticle surfaces.

Here, shown is the conjugation scheme for ovalbumin (OVA). OVA is a model protein for investigating DC antigen presentation that possesses the antigenic polypeptides $OVA_{257-264}$ and $OVA_{323-339}$ which are processed by DC through MHCI and II pathways, respectively. The conjugation scheme starts with synthesis of Pluronic divinylsulfone to which OVA is coupled via a free thiol group on OVA in a Michael addition reaction. Synthetic details for both steps are given below.

Pluronic F127 (Sigma), divinylsulfone (Fluka), sodium hydride (Aldrich), toluene (VWR), acetic acid (Fluka), diethylether (Fisher), dichloromethane (Fisher) and Celite (Macherey Nagel) were used as received. The reaction was carried under argon (Messer). $^1$H NMR was measured in deuterated chloroform (Armar) and chemical shifts (δ) are given in ppm relative to internal standard tetramethylsilane (Armar) signal at 0.0 ppm.

A solution of 15 g (1.18 mmol) of Pluronic F-127 in 400 ml toluene was dried by azeotropic distillation for 4 h using a Dean-Stark trap. The solution was cooled in an ice bath and 0.283 g (11.8 mmol) sodium hydride was added. The reaction mixture was stirred for 15 min and 3.55 ml (35.4 mmol) divinyl sulfone (Sigma-Aldrich) was added quickly. After stirring in the dark for 5 days at room temperature the reaction was quenched by adding 1.35 ml (23.6 mmol) acetic acid. After filtering over celite and concentrating the filtrate under reduced pressure to a small volume the product was precipitated in 1 liter of ice-cold diethylether. The solid was filtered off, dissolved in minimum amount of dichloromethane and precipitated in ice-cold diethylether four times in total. The polymer was dried under vacuum to yield 6.0 g and stored under argon at −20° C. prior to OVA conjugation. NMR showed the presence of vinyl sulfone and the degree of functionalization was 88%. δ=1.1 (m, $CH_3$, PPG), 3.4 (m, CH, PPG), 3.5 (m, $CH_2$, PPG), 3.6 (PEG), 6.1 (d, $CH_{cis}$=CH—$SO_2$) and 6.4 (d, $CH_{trans}$=CH—$SO_2$), 6.85 (dd, $CH_2$=$CHSO_2$—).

Prior to conjugation PLURONIC vinylsulfone was dialyzed against water using a regenerated cellulose dialysis tube with molecular weight cut off of 6-8 for kDa days. The material was recovered by lyophilization and NMR is measured to confirm that this step has no influence on the number of vinyl sulfone groups. Conjugation of OVA is done by adding 300 mg (0.023 mmol) PLURONIC vinylsulfone to a solution of 50 mg (0.0011 mmol) OVA in 0.1 M sodium phosphate buffer (pH=8.1). After reacting for 6 h at 4° C. the reaction mixture was lyophilized. Dichloromethane is added and the turbid mixture centrifuged at 12000 rpm for 5 min at room temperature. The dichloromethane, containing unreacted PLURONIC vinylsulfone, is removed and the precipitate dried under reduced pressure to remove residual dichloromethane. The PL-VS-OVA was then stored at −20° C. until used for nanoparticle synthesis.

Particles were synthesized as described herein with the difference that 2% wt of the Pluronic was replaced with PL-VS-OVA. A total amount of 1.5% PLURONIC to PPS (weight/volume) was used. In order to reduce the exposure of the protein or peptides to the basic conditions during nanoparticle synthesis reaction time was reduced to 6 h and base was added at 1:1 molar ratio to initiator-thiols.

In addition PL-VS-OVA can be fluorescently labeled with rhodamine iodoacetamide by reacting the remaining free thiols on OVA. Nanoparticles can be synthesized and labeled with flourescein iodoacetamide to produce dual labeled OVA-conjugated nanoparticles, where OVA is labeled with rhodamine and nanoparticles with fluorescein.

Dual labeled OVA-conjugated nanoparticles were injected intradermally into mice as described herein. Lymph nodes were then removed at 24 and 48 h post-injection, they were then frozen and cryosectioned. The lymph node sections were then viewed by fluorescence microscopy.

Figure 11:
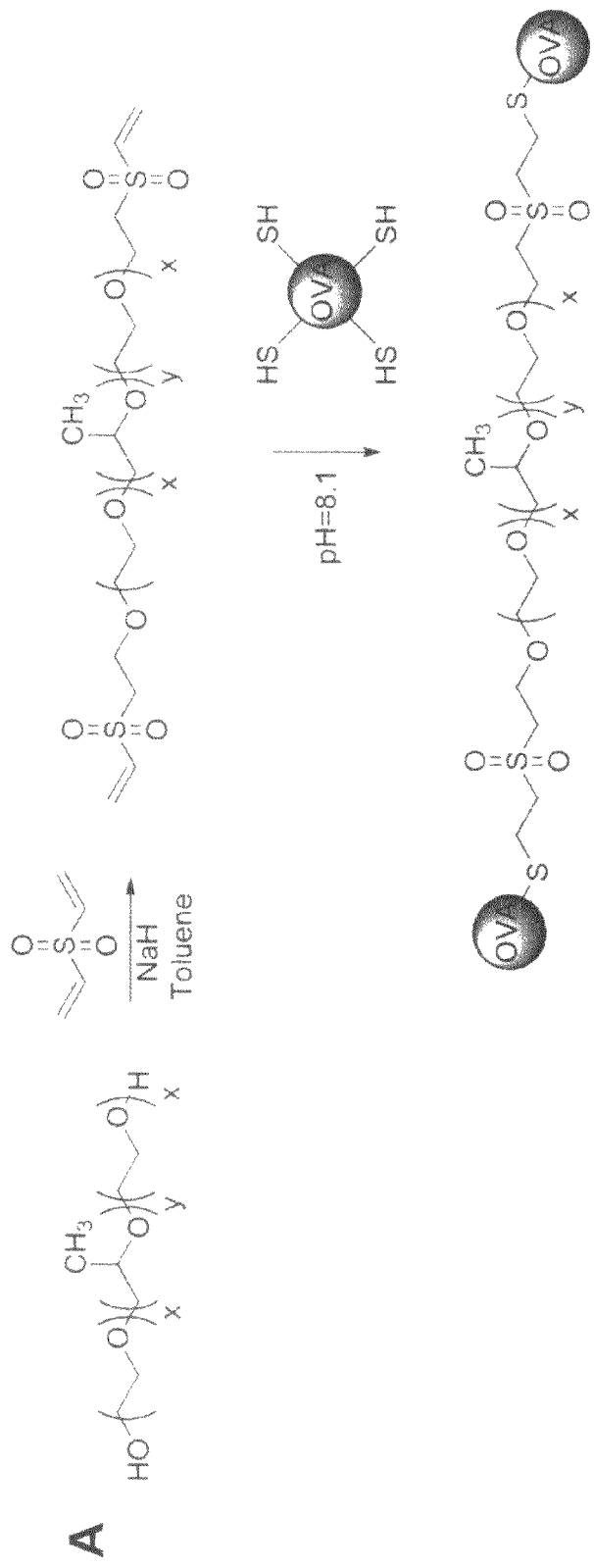
FIG. 11 shows a chemical scheme to modify nanoparticles and a photomicrograph of the same in lymph nodes, wherein at (A) PLURONIC is functionalized with vinylsulfone (PL-VS). Vinylsulfone can then be attached to the free cysteines on Ovalbumin (OVA). PL-VS-OVA is then blended with PLURONIC and 25 nm nanoparticles are synthesized as per usual. (B) 25 nm OVA-conjugated PLURONIC-stabilized nanoparticles deliver OVA to lymph nodes.
Figure 11:
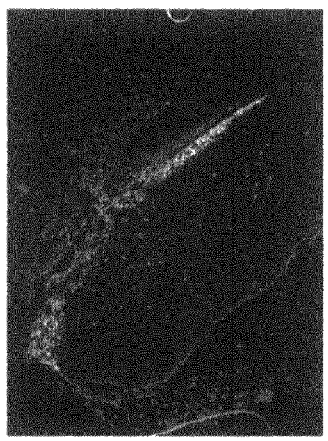
Figure 11:
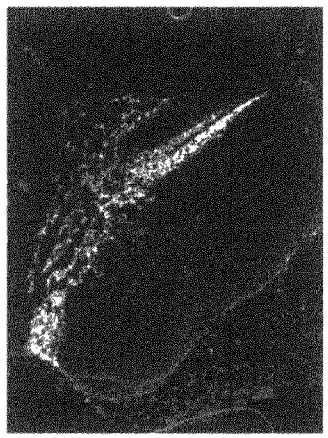

Dynamic light scattering was performed on OVA conjugated PLURONIC-stabilized nanoparticles and demonstrated that the size was maintained at ~25 nm. Dual labeled OVA-conjugated PLURONIC-stabilized nanoparticles were present in lymph nodes at 24 and 48 h post-injection, as demonstrated in FIG. 11. The OVA was present in the same locations as nanoparticles. These results demonstrate that functionalizing the nanoparticles with a protein antigen OVA of ~43 kDa MW does not significantly effect nanoparticle size. The ability to produce OVA-conjugated nanoparticles of 25 nm allows the protein antigen to be delivered via lymphatics to DCs in lymph nodes. This delivery of antigen to resident lymph node DCs offers the possibility of enhancing the subsequent adaptive immune response. OVA is presented here merely as an exemplary, model antigen. Any number of molecular antigens can be analogously utilized, including peptides, proteins, including glycopeptides, and nucleic acids that encode protein antigens.

Example 13

DC Maturation Induced by OVA Conjugated to PLURONIC-Stabilized Nanoparticles 25 nm OVA-conjugated PLURONIC-stabilized nanoparticles and OVA mixed with lipopolysaccharide (LPS) were injected intradermally into mice as described herein. Lymph nodes were then harvested and cells were isolated and stained for CD11c, CD86, CD80, and CD40 as described herein. Flow cytometry was performed to determine maturation profile of lymph node DCs.

Figure 12:
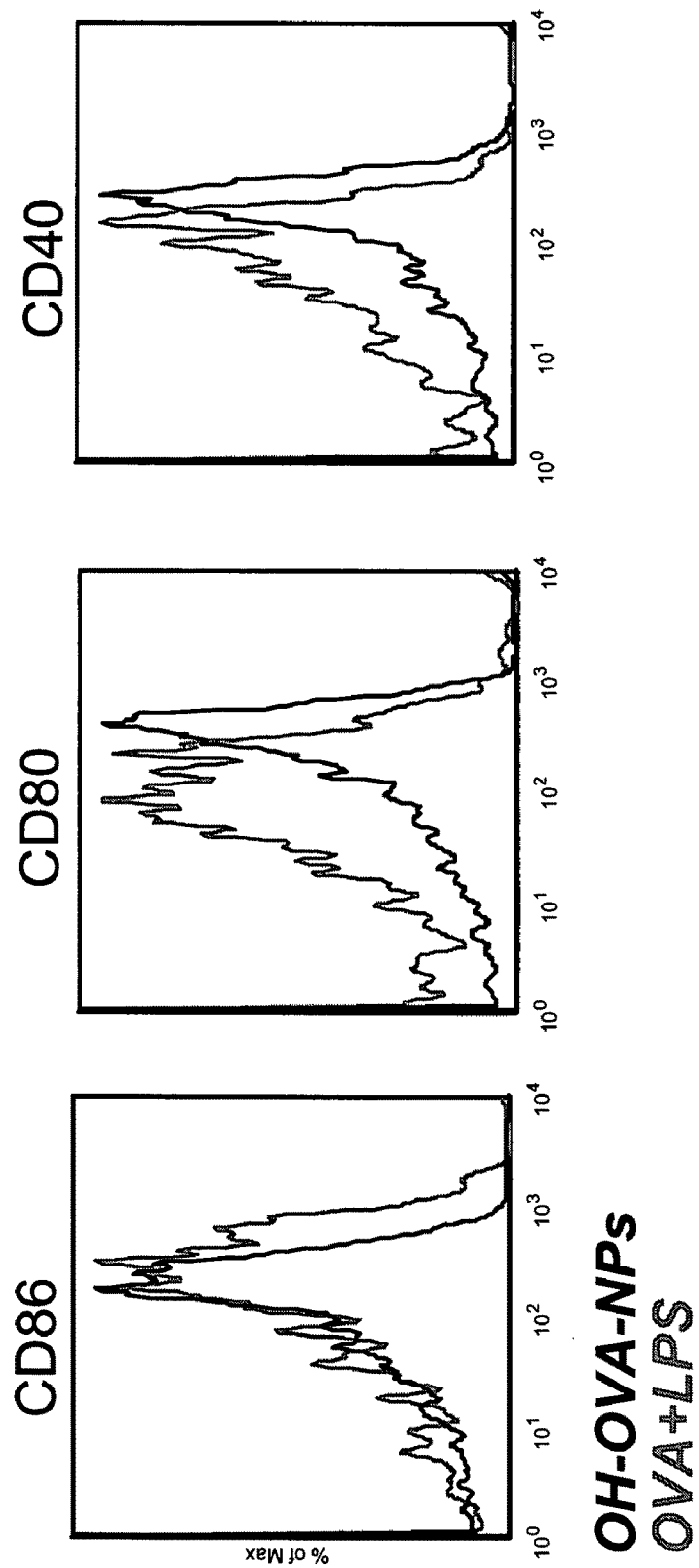
FIG. 12 depicts graphs showing that 25 nm OVA-conjugated PLURONIC-stabilized (and thus hydroxylated) complement activating PPS nanoparticles (OH-OVA-NPs) induce DC maturation to the similar levels as OVA with LPS following injections into mide at 24 hr.

As shown in FIG. 12, the CD86, CD80, and CD40 profiles for 25 nm OVA-conjugated PLURONIC-stabilized nanoparticles compared to positive control OVA with LPS are nearly the same. Both show high expression of these DC maturation markers. These results show that the DC maturation response in vivo is nearly the same for OVA delivered by PLURONIC-stabilized 25 nm nanoparticles and OVA co-injected with the molecular danger signal LPS. This suggests the possibility to use OVA conjugated to small nanoparticles, e.g. 20-45 nm, that are hydroxylated and complement-activating, e.g., formed by PLURONIC-stabilization of PPS nanoparticles, as both antigen delivery vehicles and maturation stimulus adjuvants.

Example 14

T Cell Proliferation

A method known as T cell adoptive transfer was used to measure T cell proliferation. OT-II Tg (Jackson Immunoresearch) mice are transgenic in that they have an upregulated level of OVA T cell receptor in CD4 T cells. Spleen and lymph nodes from OT-II Tg mice were isolated to make cell suspensions. For spleen cell suspensions, red blood cells were lysed with 1.667% $NH_4Cl$. Cells from spleen and lymph nodes were pooled and count: total of $400 \times 10^6$ cell recovered Cells were labeled with carboxyfluoroscein succinimidyl ester (CFSE) and re-suspended at $20 \times 10^6$/ml in RPMI w/o FBS. CFSE stock was 5 mM in DMSO. A first dilution 1/10 was made in PBS and the volume necessary was added into the cells to have a final concentration of 5 µM. CFSE was added, mixed gently and incubated with the cells at 37° C. for 10 min and left with the lid open and mixed gently about every 2 min (cells were split into 2 tubes to prevent clot formation and cell death). After incubation, RPMI with 5% FBS was added to wash the cells, washed 1× with RPMI w/o FBS and 1× with PBS. A cell count was performed after CFSE labeling for a total of $300 \times 10^6$ cells.

Cells were re-suspended in PBS at $50 \times 10^6$/ml, and $10 \times 10^6$ cells were injected (200 µl/mouse) in the tail vein of CD45.1 congenic recipient mice. A fraction of cells were kept to check by flow cytometry CFSE labeling and the proportion of CFSE+ T cells injected. Cells were stained with APC anti-CD4.

At day 2, 20 µl of antigen (OVA at 10 ug+5 ug LPS or 25 nm OVA-conjugated PLURONIC-stabilized nanoparticles at 10 ug) were injected into the front footpads of recipient mice. At day 5, mice were sacrificed and from each mouse, brachial and axillary lymph nodes were removed and pooled to make cell suspensions. The cells were stained for CD45.2 PE, propidium idodide (dead cells), and CD4 Allophycocyanin. Flow cytometry was performed to measure T cell proliferation.

Figure 13:
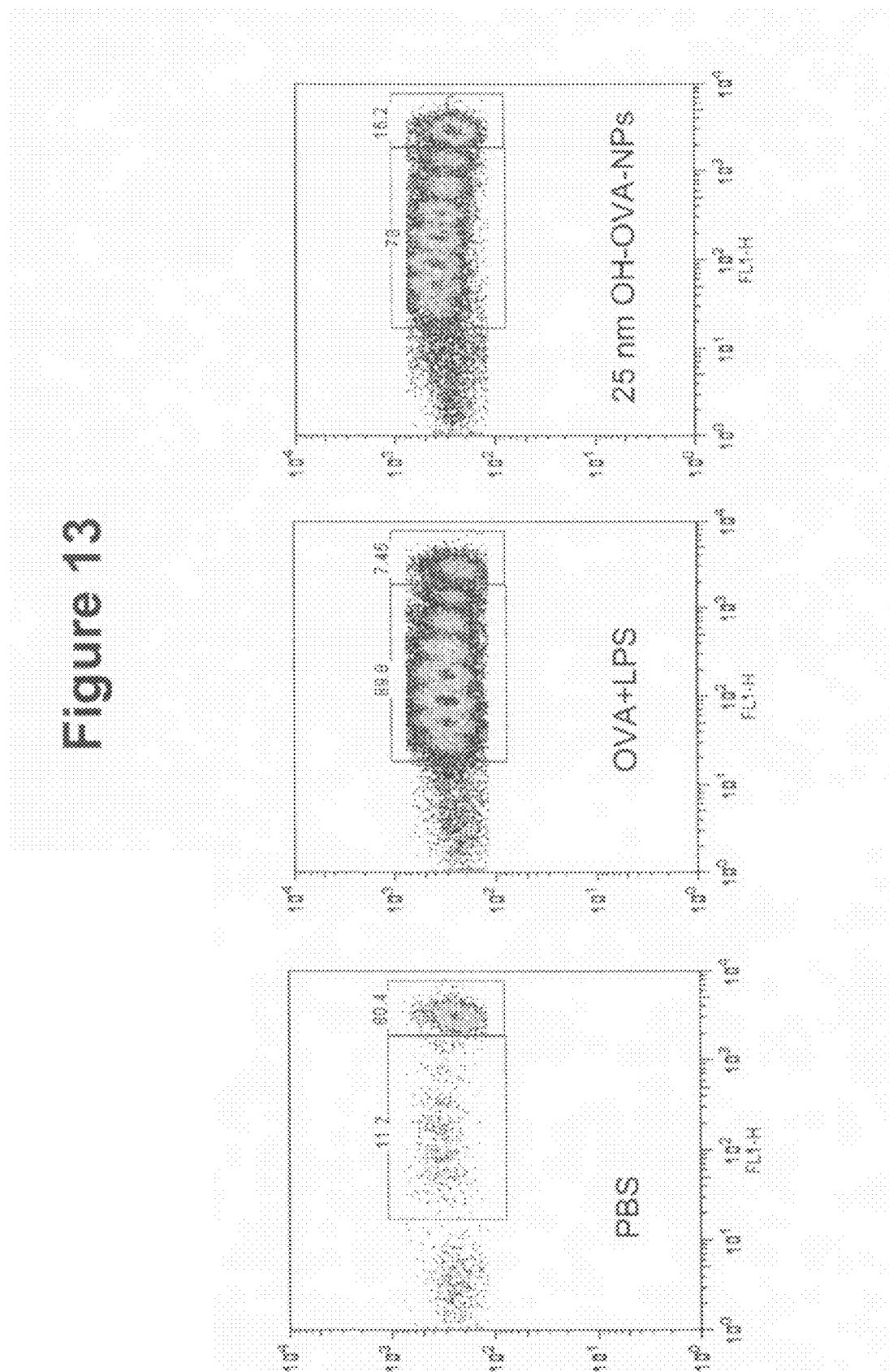
FIG. 13 depicts graphs showing that 25 nm OVA-conjugated PLURONIC-stabilized (and thus hydroxylated) complement activating nanoparticles (OH-OVA-NPs) cause CD4 T cell proliferation at same levels as OVA with LPS after adoptive transfer of T cells from OT-II mice.

FIG. 13 (left) shows that after an injection of PBS, all CFSE labeled OT-II T cells remained at a maximum fluorescence level. However, following injection of positive control OVA with LPS (center) and OVA conjugated to 25 nm PLURONIC-stabilized (and thus hydroxylated) PPS nanoparticles there is a significant decrease in fluorescence of CD4 T cells. This decrease in fluorescence is indicative of daughter populations of cells, which exhibit less fluorescence than parent populations. There were approximately 7 cycles of proliferation after injection of OVA with LPS or OVA conjugated to PLURONIC-stabilized PPS nanoparticles. OT-II mice are transgenic in that they possess CD4 T cells that upregulate T cell receptor for OVA. Therefore these T cells are extremely sensitive when they encounter the OVA antigen. Therefore, adoptive transfer of CFSE labeled OT-II T cells into WT mice is an excellent model for measuring T cell proliferation in vivo.

Herein it is demonstrated that lymph node DCs mature following delivery of OVA conjugated to 25 nm PLURONIC-stabilized (and thus hydroxylated) PPS nanoparticles. These results now show that following this internalization of nanoparticles, the OVA antigen is processed at least partially through the MHC-II pathway and its antigenic peptide is presented by mature DCs to CD4 T cells. The CD4 T cells in turn become activated and proliferate. Activated CD4 T cells are capable of helping adaptive immune responses (e.g., presenting antigen to B cells for the induction of antibody production). Our results demonstrate that OVA conjugated to 25 nm PLURONIC-stabilized (and thus hydroxylated and complement-activating) are capable of inducing T cell proliferation at very similar level as positive control OVA with LPS. This is significant as it suggests that further T cell mediated immune responses will be mounted.

Example 15

CD8 T Cell Memory—Measurements of Cellular Immunity 25 nm OVA-conjugated PLURONIC-stabilized nanoparticles, OVA in PBS, and OVA with LPS were injected into C57/BL6 mice as described herein. Mice were then given a booster injection at 7 d. At 21 d, mice were then sacrificed and lymph nodes were removed and cells were isolated as described herein. Cell suspensions were counted using a hemocytometer.

An ELISPOT plate for IFN-γ (eBioscience) was prepared according to manufacturer's protocol. RPMI media with 10% mouse serum was added to each well at 20 µl/well. Next 2 units of IL-2 and 0.4 µg of CD28 was added to each well. Next 20 µl/well of $OVA_{323-339}$ MHC-I peptide was added at 2 mM concentration. Cells were then added to the wells at 100 µl/well. Some wells received no OVA peptide, as an unstimulated control while other wells received PMA as a positive control. The plate was kept in a 37° C. incubator for 2 days. After 2 days, ELISPOT plate was developed according to manufacturer's protocol. Images of wells were taken with Leica MZ16FA stereoscope. Spots in wells were then counted with Matlab image analysis program.

Figure 14:
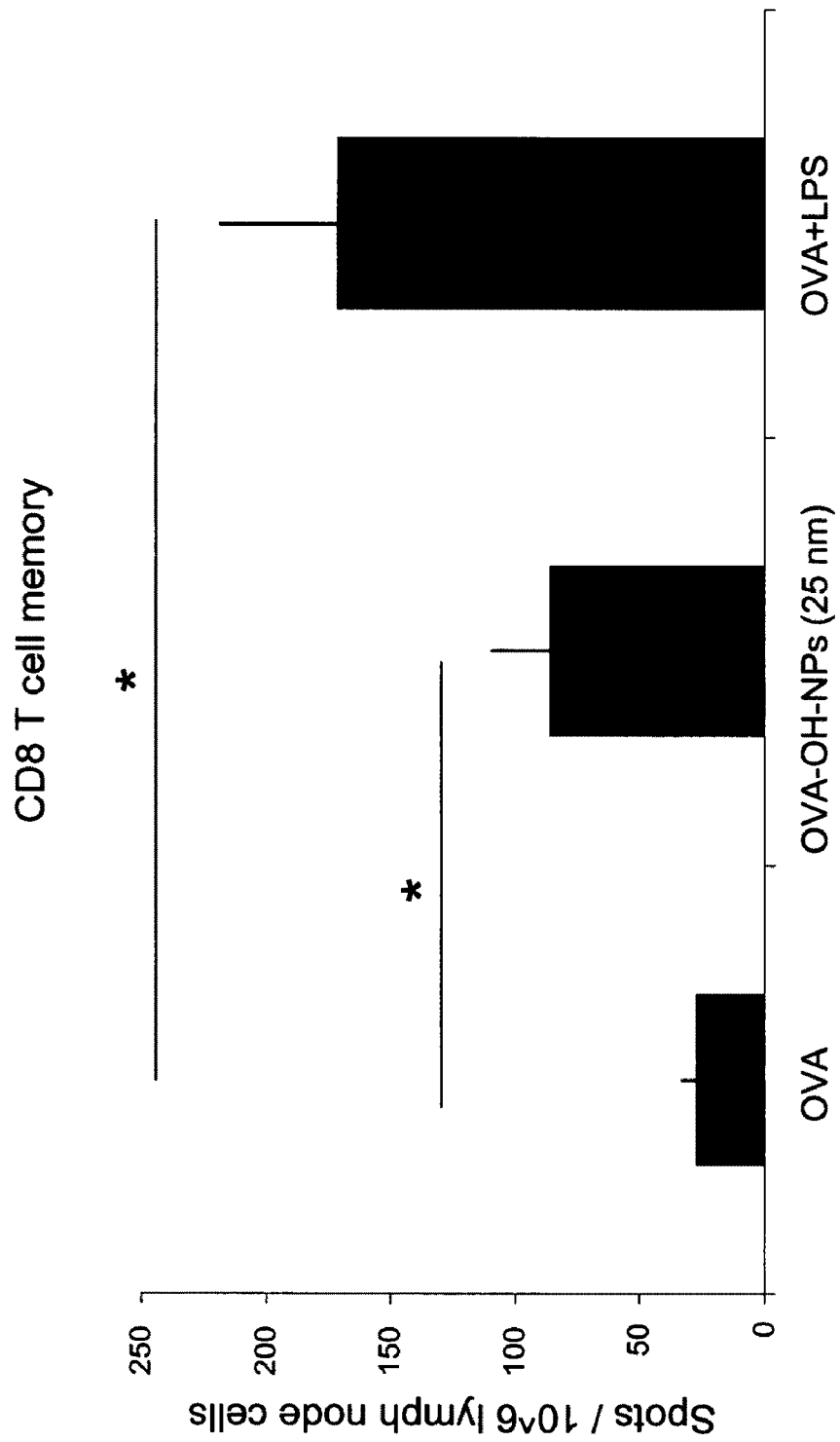
FIG. 14 depicts graphs showing that 25 nm OVA-conjugated PLURONIC-stabilized (and thus hydroxylated) complement activating nanoparticles (OH-OVA-NPs), cause CD8 T cell memory, measured through IFN-γ spots/lymph node cells. *, P<0.05.

As shown in FIG. 14, following immunization of mice, an ELISPOT assay was used to determine the amount of IFN-γ producing CD8 T cells (measured by spots on the plate) after re-exposure to antigen. Mice that received injections of OVA in PBS showed very low numbers of IFN-γ T cells, while there was a significant increase in mice injected with OVA conjugated to 25 nm PLURONIC-stabilized (and thus hydroxylated and complement-activating) nanoparticles and positive control OVA with LPS. Consistent with other results presented herein, OVA conjugated to very small nanoparticles (e.g., 20-45 nm) that are complement-activating (e.g., PLURONIC-stabilized (and thus hydroxylated) PPS nanoparticles) are capable of inducing DC maturation and CD4 T cell proliferation. Here we showed that OVA conjugated to PLURONIC-stabilized 25 nm nanoparticles can sufficiently produce CD8 T cell memory. CD8 T cells respond to antigen processed and presented by the MHC-I pathway. The MHC-I pathway is generally associated with antigen that is processed in the cytoplasm of DCs. This suggests that the nanoparticles can deliver antigen for both MHC-I and -II processing and presentation. CD8 T cells are also known as cytotoxic killer T cells as they directly attack pathogen and pathogen infected cells. Therefore the ability of small (e.g., 20-45 nm) complement activating (e.g., PLURONIC-stabilized) nanoparticles to produce CD8 T cell memory shows the strong potential for this to be used in vaccines.

Example 16

Antibody (Ab) Titers—Measurements of Humoral Immunity 25 nm OVA-conjugated PLURONIC-stabilized (and thus hydroxylated) nanoparticles, 100 nm OVA-conjugated PLURONIC-stabilized (and thus hydroxylated) nanoparticles, 25 nm OVA-conjugated methoxy-terminated PLURONIC-stabilized (and thus not hydroxylated) nanoparticles, OVA in PBS, and OVA with LPS were injected into C57/BL6 mice as described above. 25 nm OVA-conjugated PLURONIC-stabilized (and thus hydroxylated) nanoparticles and OVA with LPS were injected into C3−/− mice. Serum was isolated from blood taken from mice prior to injections and at 21 d post-injection and stored at −20° C. until used. There were no booster injections.

96 well plates (Becton Dickinson) were coated with OVA in PBS (2 µg/ml) at 100 µl/well. Plates were left overnight at room temperature (RT). Unbound antigen was flicked off and plate was washed 3× with 200 µl/well DI water. Plates were then blocked for 1.5 h at RT with 200 µl/well blocking buffer.

Mouse serum samples were diluted serially from $1:10^3$ until $1:10^8$ in blocking buffer. When plates were finished blocking, they were washed 3× with 150 µl/well wash buffer. Serum samples were then added to wells at 50 µl/well for 2 h at RT. Pre-injected serum samples were added in triplicated. Samples were then flicked out and plate was then washed with wash buffer 5× at 150 µl/well. Mouse anti-IgG-HRP was diluted in blocking buffer 1:3000 and added at 50 µl/well for 2 h at RT. HRP antibody was then flicked out and plate was washed with wash buffer 5× at 150 µl/well. Next, HRP substrate reagent (R&D systems) was added at 100 µl/well in the dark for 45 min at RT. The reaction was stopped by adding 50 µl/well of $2NH_2SO_4$. Plate absorbance was then measured on Tecan plate reader at 450 nm and 540 nm wavelength. The 540 nm background values were subtracted from 450 nm to obtain final values. A positive sample was determined if the post-injected serum value was greater than a cutoff value. The cutoff value was calculated from the pre-injected triplicate average plus standard deviation multiplied by 3. The highest dilution with a positive value is considered the antibody (Ab) titer value.

Figure 15:
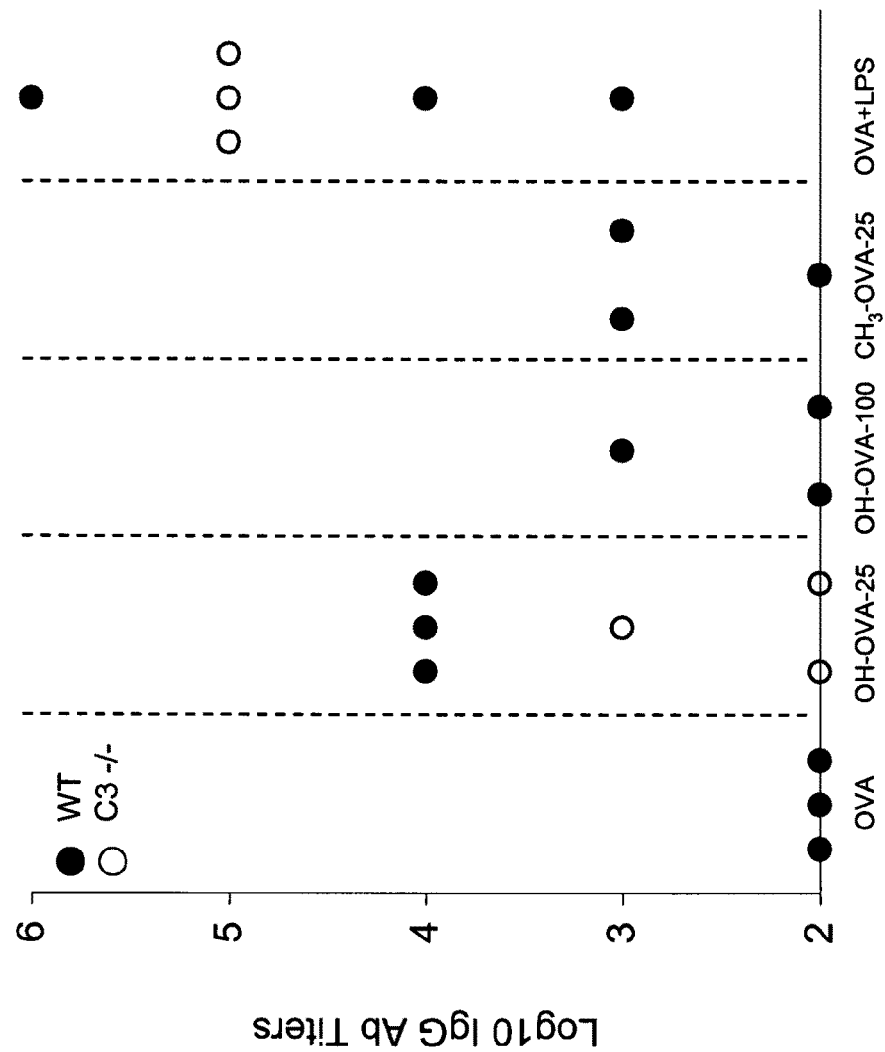
FIG. 15 depicts graphs showing OVA Ab titers at 21 days. 25 nm OVA-conjugated PLURONIC-stabilized (and thus hydroxylated) nanoparticles (OH-OVA-NPs) cause OVA Ab titers at levels similar to OVA with LPS. 25 nm OVA-conjugated methoxy-terminated PLURONIC stabilized PPS nanoparticles and 100 nm OVA-conjugated PLURONIC-stabilized (and thus hydroxylated) nanoparticles (OH-OVA-100) cause lower Ab titers. 25 nm OVA-conjugated PLURONIC-stabilized (and thus hydroxylated) (OH-OVA-25) cause lower Ab titers in C3−/− mice.

The $\log_{10}$ IgG OVA Ab titers were determined in mice injected with various treatments, as shown in FIG. 15. Mice injected with the negative control of OVA with PBS showed no positive titers. Mice injected with the positive control of OVA with LPS showed positive titers between 3-6 in both wild-type and C3−/− mice. Injections of OVA conjugated to 25 nm PLURONIC-stabilized PPS nanoparticles produced titers of 4, while injections of OVA conjugated to 100 nm PLURONIC-stabilized PPS nanoparticles and OVA conjugated to 25 nm methoxy-terminated PLURONIC-stabilized PPS nanoparticles produced lower titer values. Finally Ab titers of the animals treated with OVA conjugated to 25 nm PLURONIC-stabilized PPS nanoparticles was significantly lower in C3−/− mice.

The presence of OVA IgG Ab titers is evidence of humoral immunity. One route for this process to occur is when antigen is processed by DCs and presented to CD4 T cells, which then stimulate B cells to produce Abs against the antigen. Delivery of free protein antigen in the absence of danger signals is known to not be capable of significantly inducing humoral immunity, and our results show this as OVA in PBS does not produce positive titers. A positive control of OVA with LPS however shows significant level of titers in both wild-type and C3−/− mice. We have shown herein that OVA conjugated to 25 nm PLURONIC-stabilized (and thus hydroxylated and complement-activating) PPS nanoparticles can induce DC maturation, T cell proliferation, and CD8 T cell memory. Here we show that OVA conjugated to 25 nm PLURONIC-stabilized (and thus hydroxylated and complement-activating) nanoparticles can also induce humoral immunity by production of anti-OVA IgG titers. OVA conjugated to 100 nm PLURONIC-stabilized nanoparticles do not produce positive titers, demonstrating that lymph node targeting is crucial for nanoparticle induced humoral immunity. Also OVA conjugated to 25 nm methoxy-terminated PLURONIC-stabilized nanoparticles, which activate complement to a much lower extent, show reduced Ab titer values, proving that control of the surface chemistry is also necessary to produce such a strong immune response, mediated through complement activation. Finally it is shown that complement activation is playing a significant role in the induction of humoral immunity as OVA conjugated to 25 nm PLURONIC-stabilized PPS nanoparticles produce much lower titer values in C3−/− mice than in wild-type mice.

These results prove that nanoparticles of the various embodiments that are made as described herein that have both special size for working through lymph node targeting, and special surface chemistry, i.e., capable of complement activation (e.g., hydroxylated, obtainable by PLURONIC stabilization and other means), can be used to produce strong T cell-dependant humoral immunity with a coinjected antigen. What is demonstrated here is the case when the antigen is conjugated to the nanoparticle surface; adsorption methods for binding the antigen to the nanoparticle surface will also be effective. Coinjection of antigen with such nanoparticles should also be effective, although perhaps to a lesser extent.

Example 17

Hydrophobic Drug Loading

Loading of hydrophobic drugs, for example dexamethasone was achieved, by an adapted solvent evaporation method [132,133]. Briefly, and by way of example, the drug was added to the solvent dichloromethane (1 mg/ml). 1 ml of drug-solvent suspension was then added to 1 ml of PPS nanoparticle solution at 20 mg/ml. The emulsions were continuously stirred in the dark at room temperature in order to evaporate the solvent. Drug loading efficiency was measured by GPC.

Statistics

Statistical significance in the Examples was determined by performing a two-tailed Student's t test. Results indicate mean±SD and 3-8 experiments were performed for each condition.

REFERENCES

The following references are hereby incorporated by reference herein to the extent that they do not contradict the explicit disclosure set forth in this application.

[1] J. Banchereau, R. M. Steinman, "Dendritic cells and the control of immunity", Nature 392(6673) (1998) 245-252.

[2] J. G. Cyster, "Chemokines—Chemokines and cell migration in secondary lymphoid organs", Science 286(5447) (1999) 2098-2102.

[3] G. J. Randolph, V. Angeli, M. A. Swartz, "Dendritic-cell trafficking to lymph nodes through lymphatic vessels", Nature Reviews Immunology 5(August 2005) (2005) 617-628.

[4] L. Bonifaz, D. Bonnyay, K. Mahnke, M. Rivera, M. C. Nussenzweig, R. M. Steinman, "Efficient targeting of protein antigen to the dendritic cell receptor DEC-205 in the steady state leads to antigen presentation on major histocompatibility complex class I products and peripheral CD8 (+) T cell tolerance", Journal of Experimental Medicine 196(12) (2002) 1627-1638.

[5] L. C. Bonifaz, D. P. Bonnyay, A. Charalambous, D. I. Darguste, S. Fujii, H. Soares, M. K. Brimnes, B. Moltedo, T. M. Moran, R. M. Steinman, "In vivo targeting of antigens to maturing dendritic cells via the DEC-205 receptor improves T cell vaccination", J Exp Med 199(6) (2004) 815-824.

[6] M. J. Copland, M. A. Baird, T. Rades, J. L. McKenzie, B. Becker, F. Reck, P. C. Tyler, N. M. Davies, "Liposomal delivery of antigen to human dendritic cells", Vaccine 21(9-10) (2003) 883-890.

[7] P. Elamanchili, M. Diwan, M. Cao, J. Samuel, "Characterization of poly(D,L-lactic-co-glycolic acid) based nanoparticulate system for enhanced delivery of antigens to dendritic cells", Vaccine 22(19) (2004) 2406-2412.

[8] S. Faraasen, J. Voros, G. Csucs, M. Textor, H. P. Merkle, E. Walter, "Ligand-specific targeting of microspheres to phagocytes by surface modification with poly(L-lysine)-grafted poly(ethylene glycol) conjugate", Pharm Res 20(2) (2003) 237-246.

[9] Y. J. Kwon, E. James, N. Shastri, J. M. Frechet, "In vivo targeting of dendritic cells for activation of cellular immunity using vaccine carriers based on pH-responsive microparticles", Proc Natl Acad Sci USA 102(51) (2005) 18264-18268.

[10] Y. J. Kwon, S. M. Standley, S. L. Goh, J. M. Frechet, "Enhanced antigen presentation and immunostimulation of dendritic cells using acid-degradable cationic nanoparticles", J Control Release 105(3) (2005) 199-212.

[11] Y. J. Kwon, S. M. Standley, A. P. Goodwin, E. R. Gillies, J. M. Frechet, "Directed antigen presentation using polymeric microparticulate carriers degradable at lysosomal pH for controlled immune responses", Mol Pharm 2(1) (2005) 83-91.

[12] C. L. van Broekhoven, C. R. Parish, C. Demangel, W. J. Britton, J. G. Altin, "Targeting dendritic cells with antigen-containing liposomes: a highly effective procedure for induction of antitumor immunity and for tumor immunotherapy", Cancer Res 64(12) (2004) 4357-4365.

[13] C. Wang, Q. Ge, D. Ting, D. Nguyen, H. R. Shen, J. Z. Chen, H. N. Eisen, J. Heller, R. Langer, D. Putnam, "Molecularly engineered poly(ortho ester) microspheres for enhanced delivery of DNA vaccines", Nature Materials 3(3) (2004) 190-196.

[14] R. F. Wang, H. Y. Wang, "Enhancement of antitumor immunity by prolonging antigen presentation on dendritic cells", Nature Biotechnology 20(2) (2002) 149-154.

[15] N. S. Wilson, D. El-Sukkari, G. T. Belz, C. M. Smith, R. J. Steptoe, W. R. Heath, K. Shortman, J. A. Villadangos, "Most lymphoid organ dendritic cell types are phenotypically and functionally immature", Blood 102(6) (2003) 2187-2194.

[16] M. Sixt, N. Kanazawa, M. Seig, T. Samson, G. Roos, D. P. Reinhardt, R. Pabst, M. B. Lutz, L. Sorokin, "The conduit system transports soluble antigens from the afferent lymph to resident dendritic cells in the T cell area of the lymph node", Immunity 22(1) (2005) 19-29.

[17] D. W. Pack, "Timing is everything", Nat Mater 3(3) (2004) 133-134.

[18] H. C. Probst, J. Lagnel, G. Kollias, M. van den Broek, "Inducible transgenic mice reveal resting dendritic cells as potent inducers of CD8+ T cell tolerance", Immunity 18(5) (2003) 713-720.

[19] M. J. Copland, M. A. Baird, T. Rades, J. L. McKenzie, B. Becker, F. Reck, P. C. Tyler, N. M. Davies, "Liposomal delivery of antigen to human dendritic cells", Vaccine 21(9-10) (2003) 883-890.

[20] M. A. Swartz, "The physiology of the lymphatic system", Advanced Drug Delivery Reviews 50(1-2) (2001) 3-20.

[21] C. J. H. Porter, "Drug delivery to the lymphatic system", Critical Reviews in Therapeutic Drug Carrier Systems 14(4) (1997) 333-393.

[22] C. J. H. Porter, S. A. Charman, "Lymphatic transport of proteins after subcutaneous administration", Journal of Pharmaceutical Sciences 89(3) (2000) 297-310.

[23] M. Papisov, R. Weissleder, "Drug delivery to lymphatic tissue", Critical Reviews in Therapeutic Drug Carrier Systems 13(1-2) (1996) 57-84.

[24] C. Oussoren, J. Zuidema, D. J. A. Crommelin, G. Storm, "Lymphatic uptake and biodistribution of liposomes after subcutaneous injection 0.2. Influence of liposomal size, lipid composition and lipid dose", Biochimica Et Biophysica Acta-Biomembranes 1328(2) (1997) 261-272.

[25] A. E. Hawley, S. S. Davis, L. Ilium, "Targeting of Colloids to Lymph-Nodes—Influence of Lymphatic Physiology and Colloidal Characteristics", *Advanced Drug Delivery Reviews* 17(1) (1995) 129-148.

[26] T. M. Allen, C. B. Hansen, L. S. S. Guo, "Subcutaneous Administration of Liposomes—a Comparison with the Intravenous and Intraperitoneal Routes of Injection", *Biochimica Et Biophysica Acta* 1150(1) (1993) 9-16.

[27] S. M. Moghimi, "Modulation of lymphatic distribution of subcutaneously injected poloxamer 407-coated nanospheres: the effect of the ethylene oxide chain configuration", *Febs Letters* 545(2-3) (2003) 241-244.

[28] S. M. Moghimi, B. Bonnemain, "Subcutaneous and intravenous delivery of diagnostic agents to the lymphatic system: applications in lymphoscintigraphy and indirect lymphography", *Advanced Drug Delivery Reviews* 37(1-3) (1999) 295-312.

[29] Y. Nishioka, H. Yoshino, "Lymphatic targeting with nanoparticulate system", *Advanced Drug Delivery Reviews* 47(1) (2001) 55-64.

[30] C. Oussoren, G. Storm, "Liposomes to target the lymphatics by subcutaneous administration", *Advanced Drug Delivery Reviews* 50 (2001) 143-156.

[31] C. Oussoren, G. Storm, "Lymphatic uptake and biodistribution of liposomes after subcutaneous injection 0.3. Influence of surface modification with poly(ethyleneglycol)", *Pharmaceutical Research* 14(10) (1997) 1479-1484.

[32] S. M. Moghimi, A. E. Hawley, N. M. Christy, T. Gray, L. Illum, S. S. Davis, "Surface Engineered Nanospheres with Enhanced Drainage into Lymphatics and Uptake by Macrophages of the Regional Lymph-Nodes", *Febs Letters* 344(1) (1994) 25-30.

[33] A. E. Hawley, L. Illum, S. S. Davis, "Preparation of biodegradable, surface engineered PLGA nanospheres with enhanced lymphatic drainage and lymph node uptake", *Pharmaceutical Research* 14(5) (1997) 657-661.

[34] A. E. Hawley, L. Illum, S. S. Davis, "Lymph node localisation of biodegradable nanospheres surface modified with poloxamer and poloxamine block co-polymers", *Febs Letters* 400(3) (1997) 319-323.

[35] L. Ilium, A. E. Church, M. D. Butterworth, A. Arien, J. Whetstone, S. S. Davis, "Development of systems for targeting the regional lymph nodes for diagnostic imaging: In vivo behaviour of colloidal PEG-coated magnetite nanospheres in the rat following interstitial administration", *Pharmaceutical Research* 18(5) (2001) 640-645.

[36] C. Oussoren, M. Velinova, G. Scherphof, J. J. van der Want, N. van Rooijen, G. Storm, "Lymphatic uptake and biodistribution of liposomes after subcutaneous injection—IV. Fate of liposomes in regional lymph nodes", *Biochimica Et Biophysica Acta-Biomembranes* 1370(2) (1998) 259-272.

[37] C. Oussoren, G. Storm, "Role of macrophages in the localisation of liposomes in lymph nodes after subcutaneous administration", *International Journal of Pharmaceutics* 183(1) (1999) 37-41.

[38] D. Hawiger, K. Inaba, Y. Dorsett, M. Guo, K. Mahnke, M. Rivera, J. V. Ravetch, R. M. Steinman, M. C. Nussenzweig, "Dendritic cells induce peripheral T cell unresponsiveness under steady state conditions in vivo", *Journal of Experimental Medicine* 194(6) (2001) 769-779.

[39] A. Rehor, J. A. Hubbell, N. Tirelli, "Oxidation-sensitive polymeric nanoparticles", *Langmuir* 21(1) (2005) 411-417.

[40] A. Rehor, N. Tirelli, J. A. Hubbell, "A new living emulsion polymerization mechanism: Episulfide anionic polymerization", *Macromolecules* 35(23) (2002) 8688-8693.

[41] A. Napoli, M. Valentini, N. Tirelli, M. Muller, J. A. Hubbell, "Oxidation-responsive polymeric vesicles", *Nature Materials* 3(3) (2004) 183-189.

[42] W. L. Olszewski, "Lymph stasis pathophysiology, diagnosis and treatment", *CRC Press*, Boca Raton etc., 1991.

[43] D. A. Berk, M. A. Swartz, A. J. Leu, R. K. Jain, "Transport in lymphatic capillaries 0.2. Microscopic velocity measurement with fluorescence photobleaching", *American Journal of Physiology-Heart and Circulatory Physiology* 39(1) (1996) H330-H337.

[44] M. A. Swartz, D. A. Berk, R. K. Jain, "Transport in lymphatic capillaries 0.1. Macroscopic measurements using residence time distribution theory", *American Journal of Physiology-Heart and Circulatory Physiology* 39(1) (1996) H324-H329.

[45] M. A. Swartz, A. Kaipainen, P. A. Netti, C. Brekken, Y. Boucher, A. J. Grodzinsky, R. K. Jain, "Mechanics of interstitial-lymphatic fluid transport: theoretical foundation and experimental validation", *Journal of Biomechanics* 32(12) (1999) 1297-1307.

[46] V. Angeli, J. Llodra, J. X. Rong, K. Satoh, S. Ishii, T. Shimizu, E. A. Fisher, G. J. Randolph, "Dyslipidemia associated with atherosclerotic disease systemically alters dendritic cell mobilization", *Immunity* 21(4) (2004) 561-574.

[47] R. P. da Silva, S. Gordon, "Phagocytosis stimulates alternative glycosylation of macrosialin (mouse CD68), a macrophage-specific endosomal protein", *Biochem J* 338 (Pt 3) (1999) 687-694.

[48] C. L. Holness, R. P. da Silva, J. Fawcett, S. Gordon, D. L. Simmons, "Macrosialin, a mouse macrophage-restricted glycoprotein, is a member of the lamp/lgp family", *J Biol Chem* 268(13) (1993) 9661-9666.

[49] S. Rabinowitz, H. Horstmann, S. Gordon, G. Griffiths, "Immunocytochemical characterization of the endocytic and phagolysosomal compartments in peritoneal macrophages", *J Cell Biol* 116(1) (1992) 95-112.

[50] S. S. Rabinowitz, S. Gordon, "Macrosialin, a macrophage-restricted membrane sialoprotein differentially glycosylated in response to inflammatory stimuli", *J Exp Med* 174(4) (1991) 827-836.

[51] M. Breel, R. E. Mebius, G. Kraal, "Dendritic Cells of the Mouse Recognized by 2 Monoclonal-Antibodies", *European Journal of Immunology* 17(11) (1987) 1555-1559.

[52] K. Inaba, W. J. Swiggard, M. Inaba, J. Meltzer, A. Mirza, T. Sasagawa, M. C. Nussenzweig, R. M. Steinman, "Tissue Distribution of the Dec-205 Protein That Is Detected by the Monoclonal-Antibody Nldc-145 0.1. Expression on Dendritic Cells and Other Subsets of Mouse Leukocytes", *Cellular Immunology* 163(1) (1995) 148-156.

[53] W. P. Jiang, W. J. Swiggard, C. Heufler, M. Peng, A. Mirza, R. M. Steinman, M. C. Nussenzweig, "The Receptor Dec-205 Expressed by Dendritic Cells and Thymic Epithelial-Cells Is Involved in Antigen-Processing", *Nature* 375(6527) (1995) 151-155.

[54] W. P. Jiang, W. J. Swiggard, A. Mirza, M. Peng, R. M. Steinman, M. C. Nussenzweig, "Molecular Characterization of a 205-Kd Protein That Is Abundant on Dendritic Cells and Identified with the Nldc-145 Monoclonal-Antibody", *Journal of Cellular Biochemistry* (1995) 20-20.

[55] G. Kraal, M. Breel, M. Janse, G. Bruin, "Langerhans Cells, Veiled Cells, and Interdigitating Cells in the Mouse Recognized by a Monoclonal-Antibody", *Journal of Experimental Medicine* 163(4) (1986) 981-997.

[56] K. Mahnke, M. Guo, S. Lee, H. Sepulveda, S. L. Swain, M. Nussenzweig, R. M. Steinman, "The dendritic cell receptor for endocytosis, DEC-205, can recycle and enhance antigen presentation via major histocompatibility complex class II-positive lysosomal compartments", *Journal of Cell Biology* 151(3) (2000) 673-683.

[57] Y. Tabata, Y. Ikada, "Phagocytosis of Polymer Microspheres by Macrophages", *Advances in Polymer Science* 94 (1990) 107-141.

[100] S. Cerritelli, A. Fontana, D. Velluto, M. Adrian, J. Dubochet, P. De Maria, J. A. Hubbell, "Thermodynamic and kinetic effects in the aggregation behavior of a poly (ethylene glycol-b-propylene sulfide-b-ethylene glycol) ABA triblock copolymer", *Macromolecules* 38(18) (2005) 7845-7851.

[102] A. Napoli, N. Tirelli, G. Kilcher, J. A. Hubbell, "New synthetic methodologies for amphiphilic multiblock copolymers of ethylene glycol and propylene sulfide", *Macromolecules* 34(26) (2001) 8913-8917.

[103] A. Napoli, N. Tirelli, E. Wehrli, J. A. Hubbell, "Lyotropic behavior in water of amphiphilic ABA triblock copolymers based on poly(propylene sulfide) and poly(ethylene glycol)", *Langmuir* 18(22) (2002) 8324-8329.

[104] A. Napoli, M. Valentini, N. Tirelli, M. Muller, J. A. Hubbell, "Oxidation-responsive polymeric vesicles", *Nature Materials* 3(3) (2004) 183-189.

[105] K. Kataoka, A. Harada, Y. Nagasaki, "Block copolymer micelles for drug delivery: design, characterization and biological significance", *Adv Drug Deliv Rev* 47(1) (2001) 113-131.

[106] A. N. Lukyanov, V. P. Torchilin, "Micelles from lipid derivatives of water-soluble polymers as delivery systems for poorly soluble drugs", *Adv Drug Deliv Rev* 56(9) (2004) 1273-1289.

[107] H. Otsuka, Y. Nagasaki, K. Kataoka, "PEGylated nanoparticles for biological and pharmaceutical applications", *Adv Drug Deliv Rev* 55(3) (2003) 403-419.

[108] D. E. Discher, A. Eisenberg, "Polymer vesicles", *Science* 297(5583) (2002) 967-973.

[109] H. Lee, I. H. Jang, S. H. Ryu, T. G. Park, "N-terminal site-specific mono-PEGylation of epidermal growth factor", *Pharm Res* 20(5) (2003) 818-825.

[110] H. Lee, T. G. Park, "Preparation and characterization of mono-PEGylated epidermal growth factor: evaluation of in vitro biologic activity", *Pharm Res* 19(6) (2002) 845-851.

[111] M. J. Roberts, M. D. Bentley, J. M. Harris, "Chemistry for peptide and protein PEGylation", *Adv Drug Deliv Rev* 54(4) (2002) 459-476.

[112] C. A. Janeway, "Immunobiology 5 the immune system in health and disease", Churchill Livingstone, Edinburgh, 2001.

[113] L. C. Bonifaz, D. P. Bonnyay, A. Charalambous, D. I. Darguste, S. Fujii, H. Soares, M. K. Brimnes, B. Moltedo, T. M. Moran, R. M. Steinman, "In vivo targeting of antigens to maturing dendritic cells via the DEC-205 receptor improves T cell vaccination", *J Exp Med* 199(6) (2004) 815-824.

[114] D. Hawiger, K. Inaba, Y. Dorsett, M. Guo, K. Malinke, M. Rivera, J. V. Ravetch, R. M. Steinman, M. C. Nussenzweig, "Dendritic cells induce peripheral T cell unresponsiveness under steady state conditions in vivo", *Journal of Experimental Medicine* 194(6) (2001) 769-779.

[115] C. L. van Broekhoven, C. R. Parish, C. Demangel, W. J. Britton, J. G. Altin, "Targeting dendritic cells with antigen-containing liposomes: a highly effective procedure for induction of antitumor immunity and for tumor immunotherapy", *Cancer Res* 64(12) (2004) 4357-4365.

[116] T. Fifis, A. Gamvrellis, B. Crimeen-Irwin, G. A. Pietersz, J. Li, P. L. Mottram, I. F. McKenzie, M. Plebanski. "Size dependant immunogenicity: therapeutic and protective properties of nano-vaccines against tumors", *J Immunol* 173 (2004) 3148-3154.

[117] M. Gadjeva, A. W. Dodds, A. Taniguchi-Sidle, A. C. Willis, D. E. Isenman, S. K. A. Law. "The covalent binding reaction of complement component C3", *J Immunol* 161 (1998) 985-990.

[118] A. Kidane and K. Park. "Complement activation by PEO-grafted glass surfaces", *J Biomed Mat Res* 48 (1999) 640-647.

[119] D. T. O'Hagan and N. M. Valiante. "Recent advances in the discover and delivery of vaccine adjuvants", *Nat Rev Drug Disc* 2 (2003) 727-738.

[120] R. J. Ulevitch. "Therapeutics targeting the innate immune system", *Nat Rev Immunol* 4 (2004) 512-520.

[121] A. Pashine, N. M. Valiante, J. B. Ulmer. "Targeting the innate immune response with improved vaccine adjuvants", *Nat Med* 11(4) (2005) 563-568.

[122]. Janeway, C. A. "Immunobiology 5 the immune system in health and disease" (Churchill Livingstone, Edinburgh, 2001).

[123] Larsen, C. P. et al. "Long-term acceptance of skin and cardiac allografts after blocking CD40 and CD28 pathways". *Nature* 381 (1996), 434-8.

[124] Hackstein, H. & Thomson, A. W. "Dendritic cells: emerging pharmacological targets of immunosuppressive drugs". *Nat Rev Immunol* 4 (2004), 24-34.

[125] Duperrier, K. et al. "Immunosuppressive agents mediate reduced allostimulatory properties of myeloid-derived dendritic cells despite induction of divergent molecular phenotypes". *Mol Immunol* 42 (2005), 1531-40.

[126] Piemonti, L. et al. "Glucocorticoids affect human dendritic cell differentiation and maturation". *J Immunol* 162 (1999), 6473-81.

[127] K. Duperrier, A. Farre, J. Bienvenu, N. Bleyzac, J. Bernaud, L. Gebuhrer, D. Rigal, A. Eljaafari, "Cyclosporin A inhibits dendritic cell maturation promoted by TNF-alpha or LPS but not by double-stranded RNA or CD40L", *J Leukoc Biol* 72(5) (2002) 953-961.

[128] J. I. Lee, R. W. Ganster, D. A. Geller, G. J. Burckart, A. W. Thomson, L. Lu, "Cyclosporine A inhibits the expression of costimulatory molecules on in vitro-generated dendritic cells: association with reduced nuclear translocation of nuclear factor kappa B", *Transplantation* 68(9) (1999) 1255-1263.

[129] A. Panhans-Gross, N. Novak, S. Kraft, T. Bieber, "Human epidermal Langerhans' cells are targets for the immunosuppressive macrolide tacrolimus (FK506)", *J Allergy Clin Immunol* 107(2) (2001) 345-352.

[130] G. Szabo, C. Gavala, P. Mandrekar, "Tacrolimus and cyclosporine A inhibit allostimulatory capacity and cytokine production of human myeloid dendritic cells", *J Investig Med* 49(5) (2001) 442-449.

[131] A. M. Woltman, J. W. de Fijter, S. W. Kamerling, L. C. Paul, M. R. Daha, C. van Kooten, "The effect of calcineurin inhibitors and corticosteroids on the differentiation of human dendritic cells", *Eur J Immunol* 30(7) (2000) 1807-1812.

[132] G. Kwon, M. Naito, M. Yokoyama, T. Okano, Y. Sakurai, K. Kataoka, "Block copolymer micelles for drug delivery: loading and release of doxorubicin", *Journal of Controlled Release* 48 (1997) 195-201.

[133] G. S. Kwon, M. Naito, M. Yokoyama, T. Okano, Y. Sakurai, K. Kataoka, "Physical entrapment of adriamycin in AB block copolymer micelles", *Pharm Res* 12(2) (1995) 192-195.

[134] M. B. Villiers, C. L. Villiers, A. M. Laharie, P. N. Marche, "Different stimulating effects of complement C3b and complete Freund's adjuvant on antibody response", *Immunopharmac* 42 (1999) 151-157.

[135] P. W. Dempsey, M. E. Allison, S. Akkaraju, C. C. Goodnow, D. T. Fearon, "C3d of complement as a molecular adjuvant: bridging innate and acquired immunity", *Science* 271(5247) (1996) 348-350.

[136] K. M. Haas, F. R. Toapanta, J. A. Olivier, J. C. Poe, J. H. Weis, D. R. Karp, J. F. Bower, T. M. Ross, T. F. Tedder. "C3d functions as a molecular-adjuvant in the absence of CD21/35 expression", *J Immunol* 172(10) (2004) 5833-5837.

[137] C. H. Nielsen, E. M. Fischer, R. G. Q. Leslie. "The role of complement in the acquired immune response", *Immunology* 100 (2000) 4-12.

[138] M. Kopf, B. Abel, A. Gallimore, M. Carroll, M. F. Bachmann. "Complement component C3 promotes T-cell priming and lung migration to control acute influenza virus infection", *Nat Med* 8(4) (2002) 373-378.

[139] T. Segura, L. D. Shea. "Surface tethered DNA complexes for enhanced gene delivery", *Bioconj Chem*, 13(3) (2002) 621-629.

[140] D. Putnam. "Polymers for gene delivery across length scales", *Nat Mat*, 5 (2006) 439-451.

[141] H. Kobayashi, M. W. Brechbiel. "Nano-sized MRI contrast agents with dendrimer cores", *Adv Drug Delivery Rev.* 57 (2005) 2271-2286.

[142] T. Dutta, N. K. Jain. "Targeting potential and anti-HIV activity of lamivudine loaded mannoxylated poly(propyleneimine) dendrimer". *Biochim Biophys Acta* xx (2007) xxx-xxx.

[143] A. K. Patri, A. Myc, J. Beals, T. P. Thomas, N. H. Bander, J. R. Baker. "Synthesis and in vitro testing of J591 antibody-dendrimer conjugates for targeted prostate cancer therapy". *Bioconjugate Chem* 15 (2004) 1174-1181.

[144] C. Plank, K. Mechtler, F. C. Szoka, E. Wagner. "Activation of the complement system by synthetic DNA complexes: a potential barrier for intravenous gene delivery". *Hum. Gene Ther.* 7 (1996) 1437-1446.

[145] R. Duncan, L. Isso. "Dendrimer biocompatibility and toxicity". *Adv. Drug Delivery Rev.* 57 (2005) 2215-2237.

It is claimed:

1. A nanoparticle composition comprising: an isolated collection of synthetic particles that comprise a synthetic polymer that comprises hydroxyl groups effective to activate complement as measurable by at least a 10-fold increase in C3a when the particles are incubated with human serum, wherein the collection has a mean particle diameter of about 10 nm to about 100 nm, and the particles are further associated with an antigen, with the isolated collection of synthetic particles being effective in the absence of adjuvants to induce T cell dependent humoral immunity in a patient against the antigen in vivo.

2. The composition of claim 1, wherein the antigen is covalently bound to the particle.

3. The composition of claim 1, wherein the isolated collection of particles is free of sequences of amino acids or sequences of saccharides that activate complement.

4. The composition of claim 1, wherein the synthetic polymer comprises a hydrophobic portion that is adsorbed to a hydrophobic portion of a second biodegradable polymer that forms a core of the nanoparticle to thereby bind the synthetic polymer to the core with the hydroxyl groups being available for interaction to activate complement.

5. The composition of claim 4, wherein the hydroxyl groups are the termini of the synthetic polymer, and wherein the synthetic polymer comprises polyalkylene oxide.

6. The composition of claim 4, wherein the synthetic polymer is a copolymer of poly(ethylene glycol)-poly(propylene glycol)-poly(ethylene glycol).

7. The composition of claim 4, wherein the second polymer is polypropylene sulfide.

8. The composition of claim 1, wherein the particles are free of targeting ligands that specifically bind to a cell.

9. The composition of claim 1, wherein the antigen is an antigen of a tumor for tumor immunotherapy or an antigen of an infectious disease.

10. The composition of claim 1, with the particles further comprising a danger signal chosen from the group consisting of inflammatory cytokines and ligands for Toll-like receptors.

11. The composition of claim 1, wherein the antigen is a polypeptide or glycopeptide antigen.

12. The composition of claim 1, wherein the collection has a mean particle diameter of about 10 nm to about 50 nm.

13. The composition of claim 12, wherein the particles are free of targeting ligands that specifically bind to a cell, the antigen is an antigen for tumor immunotherapy or infectious disease, and further comprising a danger signal chosen from the group consisting of inflammatory cytokines and ligands for Toll-like receptors.

14. The composition of claim 12, wherein the synthetic polymer comprises an amphiphilic block copolymer of at least one hydrophobic block and at least one hydrophilic block, wherein the block copolymer self-assembles in aqueous solutions to form the particles, wherein the functional groups on the hydrophilic block provide the activation of complement.

15. The composition of claim 14, wherein the hydrophilic block comprises polyethylene glycol terminated with the hydroxyl groups.

16. A method of making an immunotherapeutic composition of nanoparticles that generate antibodies in a patient against an antigen comprising emulsion polymerization of a first polymer with a second polymer that is the emulsifier used during the polymerization to make a collection of particles with a mean diameter of between 20 and 50 nm, choosing the second polymer to comprise hydroxyl functional groups that activate complement measurable by at least a 10-fold increase in C3a when the particles are incubated with human serum, and associating an immunotherapeutic antigen with the particles, with the antigen being chosen for the generation of antibodies by a patient against the antigen.

17. The method of claim 16, wherein the first polymer is biodegradable.

18. A method of delivering an immunotherapeutic agent to stimulate an immune system of a patient, the method comprising
introducing into the patient a collection of synthetic particles that
activate complement in the patient,
comprise the immunotherapeutic agent, and
deliver the immunotherapeutic agent to antigen-presenting cells,
wherein
the particles comprise a first polymer that activates complement as measurable by at least a 10-fold increase in C3a when the particles are incubated with human serum, the collection has a mean diameter from about 10 nm to about 50 nm,
and
the particles comprise a second polymer to which the first polymer is bound.

19. The method of claim 18, wherein the second polymer is biodegradable.

20. The method of claim 18, wherein the particles are free of cell-specific targeting ligands and are specifically targeted to antigen presenting cells in lymph nodes for delivery of the immunotherapeutic agent to the antigen-presenting cells.

21. A nanoparticle composition comprising:
an isolated collection of synthetic particles, wherein the collection has a mean diameter of about 10 nm to about 100 nm, wherein the particles comprise
hydroxyl groups effective to activate complement as measurable by at least a 10-fold increase in C3a when the particles are incubated with human serum, and
an immunosuppressant drug,
wherein the particles are further associated with an antigen for antigen-specific tolerance.

22. The composition of claim 21, wherein the particles comprise an amphiphilic block copolymer of at least one hydrophobic block and at least one hydrophilic block, wherein the block copolymer self-assembles in aqueous solutions to form the particles.

23. The composition of claim 21, wherein the collection has a mean particle diameter of about 10 nm to about 50 nm.

24. The method of claim 18 wherein the immunotherapeutic agent is an antigen chosen for generation of antibodies against the antigen.

25. The method of claim 24 wherein the antigen is chosen to be an antigen of a tumor for tumor immunotherapy or an antigen of an infectious disease and further comprising administration of the nanoparticles as needed to maintain a desired titer of antibodies.

26. The method of claim 18, wherein the antigen is covalently bound to the particle.

27. The method of claim 18, wherein the isolated collection of particles is chosen to be free of sequences of amino acids or sequences of saccharides that activate complement.

28. The method of claim 18, wherein the nanoparticles comprise a hydrophobic core and a polymer that has a first hydrophobic portion that is adsorbed to the core and a second portion with the hydroxyl groups disposed to be available to activate complement.

29. The method of claim 18, wherein the particles are free of targeting ligands that specifically bind to a cell.

30. The method of claim 18 wherein the immunotherapeutic agent comprises an immunosuppressant.

31. The method of claim 18 wherein the immunotherapeutic agent comprises an antigen for antigen-specific tolerance.

* * * * *